United States Patent
Bhat et al.

(10) Patent No.: US 7,569,686 B1
(45) Date of Patent: Aug. 4, 2009

(54) COMPOUNDS AND METHODS FOR SYNTHESIS OF BICYCLIC NUCLEIC ACID ANALOGS

(75) Inventors: Balkrishen Bhat, Carlsbad, CA (US); Jie Xia, Carlsbad, CA (US); Punit P. Seth, San Marcos, CA (US); Guillermo Vasquez, Oceanside, CA (US); Michael T. Migawa, Carlsbad, CA (US); Charles Allerson, San Diego, CA (US); Thazha P. Prakash, Carlsbad, CA (US); Eric E. Swayze, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 225 days.

(21) Appl. No.: 11/747,042

(22) Filed: May 10, 2007

Related U.S. Application Data

(63) Continuation-in-part of application No. 11/627,964, filed on Jan. 27, 2007, now Pat. No. 7,399,845.

(60) Provisional application No. 60/747,068, filed on May 11, 2006, provisional application No. 60/762,722, filed on Jan. 27, 2006, provisional application No. 60/805,660, filed on Jun. 23, 2006.

(51) Int. Cl.
C07H 21/00 (2006.01)

(52) U.S. Cl. .................... 536/25.3; 536/18.1; 536/18.5; 536/18.6; 536/22.1

(58) Field of Classification Search .................. None
See application file for complete search history.

(56) References Cited

U.S. PATENT DOCUMENTS

| | | |
|---|---|---|
| 3,687,808 A | 8/1972 | Merigan, Jr. et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |

(Continued)

FOREIGN PATENT DOCUMENTS

| | | |
|---|---|---|
| WO | WO 99/14226 A2 | 3/1999 |
| WO | WO 2005/121371 A2 | 12/2005 |

OTHER PUBLICATIONS

Babu et al. J. Chem. Soc., Perkin Trans. 1 (2002), pp. 2509-2519.*

(Continued)

*Primary Examiner*—Patrick T Lewis
(74) *Attorney, Agent, or Firm*—Jones Day

(57) ABSTRACT

The present invention provides compounds and methods of using them for preparing bicyclic nucleosides. The bicyclic nucleosides are useful for preparing chemically modified oligomeric compounds. Oligomeric compounds comprising these bicyclic nucleosides have enhanced properties such as increased nuclease resistance.

26 Claims, No Drawings

U.S. PATENT DOCUMENTS

| | | |
|---|---|---|
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer et al. |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,600,032 B1 | 7/2003 | Manoharan et al. |
| 6,770,748 B2 | 8/2004 | Imanishi et al. |
| 6,794,499 B2 | 9/2004 | Wengel et al. |
| 2003/0082807 A1 | 5/2003 | Wengel |
| 2003/0087230 A1 | 5/2003 | Wengel |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0143114 A1 | 7/2004 | Imanishi et al. |
| 2004/0192918 A1 | 9/2004 | Imanishi et al. |
| 2004/0219565 A1 | 11/2004 | Kauppinen et al. |

OTHER PUBLICATIONS

Beaucage, S. L. et al., "Advances in the Synthesis of Oligonucleotides by the Phosphoramidite Approach," *Tetrahedron* (1992) 48(12):2223-2311.

Beaucage, S. L. et al., "The Functionalization of Oligonucleotides Via Phosphoramidite Derivatives," *Tetrahedron* (1993) 49(10):1925-1963.

Beaucage S. L. et al., "The Synthesis of Specific Ribonucleotides and Unrelated Phosphorylated Biomolecules by the Phosphoramidite Method," *Tetrahedron* (1993) 49(46):10441-10488.

Koshkin, A. A. et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron* (1998) 54:3607-3630.

Kumar, R. et al., "The First Analogues of LNA (Locked Nucleic Acids): Phosphorothioate-LNA and 2'-Thio-LNA," *Bioorg. Med. Chem. Lett.* (1998) 8:2219-2222.

Singh, S. K. et al., "LNA (locked nucleic acids): synthesis and high-affinity nucleic acid recognition," *Chem. Commun.* (1998) 455-456.

Singh, S. K. et al., "Synthesis of 2'-Amino-LNA: A Novel Conformationally Restricted High-Affinity Oligonucleotide Analogue with a Handle," *J. Org. Chem.* (1998) 63(26):10035-39.

Wahlestedt, C. et al., "Potent and nontoxic antisense oligonucleotides containing locked nucleic acids," *PNAS* (2000) 97(10):5633-5638.

* cited by examiner

COMPOUNDS AND METHODS FOR SYNTHESIS OF BICYCLIC NUCLEIC ACID ANALOGS

CROSS-REFERENCE TO RELATED APPLICATIONS

The present application: claims benefit under 35 USC 119(e) to U.S. Provisional Ser. No. 60/747,068 filed May 11, 2006, and is a continuation-in-part of U.S. Ser. No. 11/627,964 filed Jan. 27, 2007, which claims the benefit of priority under 35 USC 119(e) to U.S. Provisional Ser. No. 60/762,722, filed Jan. 27, 2006, and U.S. Provisional Ser. No. 60/805,660, filed Jun. 23, 2006, each of which is incorporated herein by reference in its entirety.

FIELD OF THE INVENTION

The present invention provides methods for the preparation of bicyclic nucleosides and compounds useful in these methods. In particular, the compounds and methods are useful for the preparation of bicyclic nucleosides comprising a bridge between the 4' and 2' ring carbon atoms. The bicyclic nucleosides are useful in one aspect for preparing oligomeric compounds.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039; also see U.S. Pat. Nos. 6,770,748, 6,268,490 and 6,794,499 and published U.S. applications 20040219565, 20040014959, 20030207841, 20040192918, 20030224377, 20040143114, 20030087230 and 20030082807. Consequently, there remains a long-felt need for modified nucleosides such as bicyclic nucleosides for use in agents that specifically regulate gene expression via antisense mechanisms. Disclosed herein are compounds and methods for the preparation of BNA's that can be incorporated into oligomeric compounds. Such oligomeric compounds are useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit a plurality of bicyclic nucleosides for these uses.

BRIEF SUMMARY OF THE INVENTION

The present invention provides compounds and methods for using these compounds for preparing bicyclic nucleosides. In one aspect the compounds have formula I:

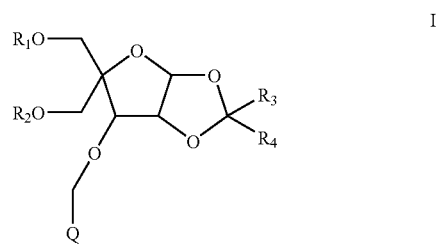

wherein:

$R_1$ is H or a hydroxyl protecting group;

$R_2$ is H or a hydroxyl protecting group;

$R_3$ and $R_4$ are each independently $C_1$-$C_6$ alkyl or substituted $C_1$-$C_6$ alkyl; and Q is a substituted phenyl or an optionally substituted polycyclylic aromatic or heteroaromatic radical.

In one embodiment Q is substituted phenyl wherein preferred positions for substitution are at one or more meta and para positions. Preferred groups for substitution include electron withdrawing groups wherein preferred electron withdrawing groups include alkoxy, thioalkoxy, substituted acyl, thiol, halogen, cyano, said substitutent groups are selected from alkyl, alkoxy, halo, acylamino (—N(H)C(=O)alkyl), phenyl or substituted phenyl. In one embodiment the substituted phenyl is 4-methoxybenzyl, 3,4-dimethoxybenzyl, 4-phenylbenzyl, 4-phenyl-3-chlorobenzyl, 4-acetylaminobenzyl or 4-azidobenzyl.

In one embodiment Q is an optionally substituted polycyclylic aromatic or heteroaromatic radical. Preferred optionally substituted polycyclylic aromatic or heteroaromatic radical comprises from 2 to about 5 fused rings. In one embodiment Q comprises two fused rings. In another embodiment Q comprises at least one heteroaromatic ring. In a further embodiment Q comprises two fused aromatic rings including only carbon and hydrogen atoms. One preferred Q is 2-naphthalenyl. In other embodiments Q is pyrenyl, purinyl, acridinyl, xanthenyl, fluorenyl, phenanthrenyl, anthracenyl, quinolinyl, isoquinolinyl, naphthalenyl, perylenyl, phenanthridinyl, phenazinyl, anthraquinonyl, azulenyl or dibenzofuranyl.

In one embodiment each $R_1$ and $R_2$ is H. In another embodiment each $R_1$ and $R_2$ is a hydroxyl protecting group. In a further embodiment one of $R_1$ and $R_2$ is H and the other of $R_1$ and $R_2$ is a hydroxyl protecting group.

In one embodiment $R_3$ and $R_4$ are each, independently, $C_1$-$C_6$ alkyl. In another embodiment $R_3$ and $R_4$ are each methyl.

In one embodiment $R_1$ is a hydroxyl protecting group, $R_2$ is H, and $R_3$ and $R_4$ are each methyl. In another embodiment $R_1$ is a hydroxyl protecting group, $R_2$ is H, $R_3$ and $R_4$ are each methyl and Q is 2-napthalenyl.

In one embodiment the compound having formula I has the configuration:

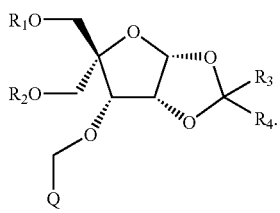

In another embodiment the compound having formula I having the above configuration is:

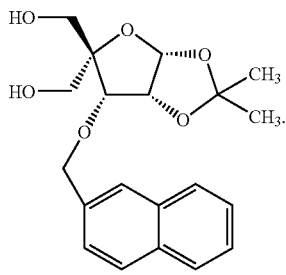

In one embodiment the compound having formula I has the configuration:

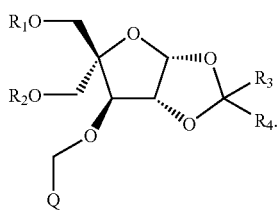

In another embodiment the compound having formula I having the above configuration is:

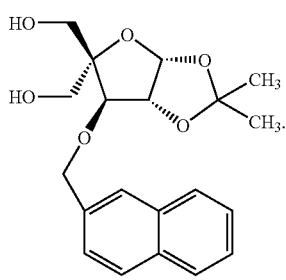

The present invention also provides methods of preparing bicyclic nucleosides comprising a bridge between the 4' and 2' ring carbons using the compound of formula I. In another embodiment the bridge comprises from 2 to 3 bivalent subunits. In a further embodiment the bivalent subunits are each, independently, selected from —$CR_5R_6$—, —C(=O)—, —$NR_5$, and —O—, wherein each $R_5$ and $R_6$ is, independently, H or $C_1$-$C_6$ alkyl, substituted $C_1$-$C_6$ alkyl, a substituted heteroatom (O, S or N) or a protecting group. In an even further embodiment the bivalent subunits form a bridge having the formula:

—$CH_2$—O—, —$(CH_2)_2$—O—, —$CH_2$—O—N($R_5$)—, —$CH_2$—N($R_5$)—O—, $CH_2$—N($R_5$)—$CH_2$—, —CH($R_5$)—O—, —$CH_2$—N($R_5$)—N($R_5$)— or —C(=O)—N($R_5$)—$CH_2$—.

In one embodiment the method uses a compound of formula I having the configuration:

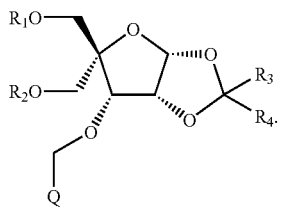

In another embodiment the method uses a compound having the configuration and formula:

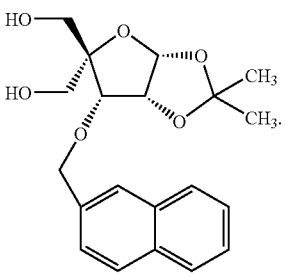

In one embodiment the method uses a compound of formula I having the configuration:

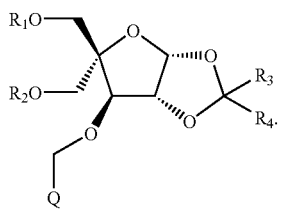

In another embodiment the method uses a compound having the configuration and formula:

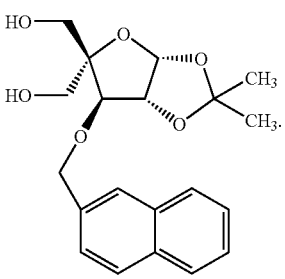

DETAILED DESCRIPTION OF THE INVENTION

The present invention provides compounds and methods useful for the preparation of bicyclic nucleosides. In particular, the compounds of the invention permit separation and purification by crystallization of downstream products formed during the preparation of BNA's thereby avoiding time consuming and more costly purification steps requiring chromatography. For example, Compound 2 and Compound 5 (see Example 1) can be isolated without chromatography due to ease of crystallization. Another advantage is that the present compounds and methods permit recovery of Compound 5 from bi-product Compound 7 (see Example 2, step B) thereby saving additional cost of raw materials.

Crystallization of compounds according to the present invention is dependent on the selection of a group Q (formula I). When Q is a monocyclic ring system such as for example phenyl (n=1, formula I) the ring is preferably substituted to influence crystallization. More preferable a bicyclic ring system or a substituted bicyclic ring system is used for Q to strongly influence the resulting compound having formula I to crystallize.

Compounds of the present invention that are useful in the synthesis of bicyclic nucleosides have formula I:

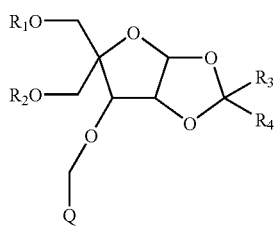

I wherein:
$R_1$ is H or a hydroxyl protecting group;
$R_2$ is H or a hydroxyl protecting group;
$R_3$ and $R_4$ are each independently $C_1$-$C_6$ alkyl or substituted $C_1$-$C_6$ alkyl; and
Q is a substituted phenyl or an optionally substituted polycylylic aromatic or heteroaromatic radical.

In one aspect of the present invention Q is a substituted phenyl ring having one or more substituent groups preferably at the meta and para positions of the ring. Some preferred substituent groups include but are not limited to alkyl, alkoxy, halo, acylamino (alkyl-C(=O)N(H)—) and phenyl. Some preferred substituted phenyl groups include but are not limited to 4-methoxybenzyl, 3,4-dimethoxybenzyl, 4-phenylbenzyl, 4-phenyl-3-chlorobenzyl, 4-acetylaminobenzyl and 4-azidobenzyl.

In another aspect of the present invention Q is an optionally substituted polycyclic aromatic or heteroaromatic radical comprising from two to about five fused or otherwise linked rings. Each ring independently comprising only carbon and hydrogen atoms or comprising one or more heteroatoms selected from O, S and N. Preferred polycyclic radicals are aromatic and comprise only C and H. A representative list of polycyclic aromatic or heteroaromatic ring systems amenable to the present invention include without limitation: pyrenes, purines, acridines, xanthenes, fluorenes, phenanthrenes, anthracenes, quinolines, isoquinolines, naphthalenes, perylenes, phenanthridines, phenazines, anthraquinones, azulenes, adamantanes and dibenzofurans. A particularly preferred polycyclic aromatic ring system is naphthalene (the preferred radical is 2-naphthalenyl).

The compounds of the present invention are useful for the synthesis of a wide variety of bicyclic nucleosides including but not limited to those having a bridge between the 4' and the 2' positions of the furanose ring wherein the bridge has the formula:

—$CH_2$—O—, —$(CH_2)_2$—O—, —$CH_2$—O—N($R_5$)—, —$CH_2$—N($R_5$)—O—, $CH_2$—N($R_5$)—$CH_2$—, —$CH(R_5)$—O—, —$CH_2$—N($R_5$)—N($R_5$)— or —C(=O)—N($R_5$)—$CH_2$— where $R_5$ is H, $C_1$-$C_6$ alkyl, substituted $C_1$-$C_6$ alkyl, a protecting group or substituted O, S or N (see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039). Examples of issued US patents and published applications include for example: U.S. Pat. Nos. 6,770,748, 6,268,490 and 6,794,499 and published U.S. applications 20040219565, 20040014959, 20030207841, 20040192918, 20030224377, 20040143114, 20030087230 and 20030082807, the text of each is incorporated by reference herein, in their entirety.

In one aspect of the present invention nucleosides are prepared having D configuration such as for example Compound 15 which is an β-D-LNA DMT phosphoramidite. In one aspect such D configured bicyclic nucleosides are prepared from compounds of the invention having the configuration:

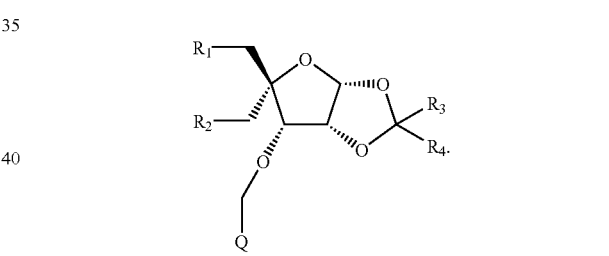

A preferred compound having this configuration has the formula:

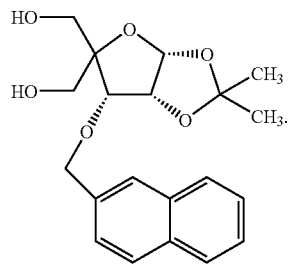

In another aspect of the present invention nucleosides are prepared having L configuration such as for example Compound 202 which is an α-L-LNA DMT phosphoramidite. In one aspect such L configured bicyclic nucleosides are prepared from compounds of the invention having the configuration:

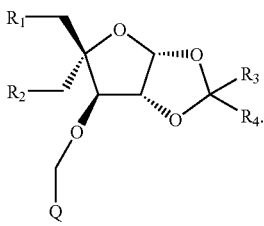

A preferred compound having this configuration has the formula:

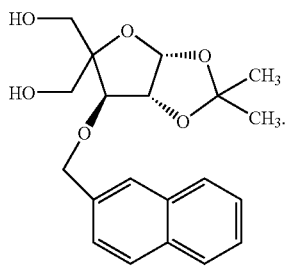

The compounds and methods of the present invention are amenable to all manner of modification as is known in the chemical arts (see for example: Richard C. Larock, Comprehensive Organic Transformations, VHC Publishers, Inc, New York (1989); Jerry March, Advanced Organic Chemistry, John Wiley & Sons, New York (1992); and Greene's Protective Groups in Organic Synthesis, 4th Edition, Greene, T. W., and Wutz, P. G. M., John Wiley & Sons, New York (2007); the text of each is incorporated by reference herein, in their entirety).

The terms "stable compound" and "stable structure" are meant to indicate a Compound that is sufficiently robust to survive isolation to a useful degree of purity from a reaction mixture, and formulation into an efficacious therapeutic agent. Only stable Compounds are contemplated herein.

Selected substituent groups within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the Compound intended. Such properties include, by way of example and not limitation, physical properties such as molecular weight, solubility or log P, application properties such as activity against the intended target, and practical properties such as ease of synthesis. Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radicals having one or more aromatic rings. Examples of aryl groups include, but are not limited to, phenyl, naphthalenyl (also referred to herein as naphthyl), tetrahydronaphthyl, indanyl, idenyl and the like. Preferred aryl ring systems have from about 5 to about 20 carbon atoms in one or more rings. Aryl groups as used herein may optionally include further substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

The term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The terms "substituted", "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxo (—O—$R_{aa}$), aryl, aralkyl, heterocyclic, heteroaryl, heteroarylalkyl, amino (—$NR_{bb}R_{cc}$), imino(=$NR_{bb}$), amido (—C(O)$NR_{bb}R_{cc}$ or —N($R_{bb}$)C(O)$R_{aa}$), azido (—$N_3$), nitro (—$NO_2$), cyano (—CN), carbamido (—OC(O)$NR_{bb}R_{cc}$ or —N($R_{bb}$)C(O) O$R_{aa}$), ureido (—N($R_{bb}$)C(O)$NR_{bb}R_{cc}$), thioureido (—N ($R_{bb}$)C(S)$NR_{bb}R_{cc}$), guanidinyl (—N($R_{bb}$)C(=$NR_{bb}$)$NR_{bb}$ $R_{cc}$), amidinyl (—C(=$NR_{bb}$)$NR_{bb}R_{cc}$ or —N($R_{bb}$)C($NR_{bb}$) $R_{aa}$), thiol (—$SR_{bb}$), sulfinyl (—S(O)$R_{bb}$), sulfonyl (—S(O)$_2$ $R_{bb}$), sulfonamidyl (—S(O)$_2NR_{bb}R_{cc}$ or —N($R_{bb}$)S(O)$_2 R_{bb}$) and conjugate groups. Wherein each $R_{aa}$, $R_{bb}$ and $R_{cc}$ is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

The term "oxo" refers to the group (=O).

The compounds (e.g., bicyclic nucleosides) described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes,* Barry M. Trost, Editor-in-Chief, Pergamon Press, New York (1993); *Advanced Organic Chemistry, Part B: Reactions and Synthesis,* 4th Ed.; Carey and Sundberg; Kluwer Academic/Plenum Publishers: New York (2001);

*Advanced Organic Chemistry, Reactions, Mechanisms, and Structure,* 2nd Edition, March, McGraw Hill (1977); *Greene's Protective Groups in Organic Synthesis,* 4th Edition, Greene, T. W., and Wutz, P. G. M., John Wiley & Sons, New York (2007); and *Comprehensive Organic Transformations,* 2nd Edition, Larock, R. C., John Wiley & Sons, New York (1999).

In one aspect of the present invention oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, drug groups such as ibuprofen, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Linking groups or bifunctional linking moieties such as those known in the art are amenable to the present invention. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glyol or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in *Greene's Protective Groups in Organic Synthesis,* 4th Edition, Greene, T. W., and Wutz, P. G. M., John Wiley & Sons, New York (2007).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, triisopropylsilyl, [(triisopropylsilyl)oxymethyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In some preferred embodiments oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725, 677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

As used herein, the term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.,* 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

The present invention provides compounds having reactive phosphorus groups useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^V$ state using known methods to yield, in preferred embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

In one aspect of the present invention bicyclic nucleosides are prepared to be incorporated into oligomeric compounds. Specific examples of some representative oligomeric compounds useful in this invention include oligonucleotides containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids et al. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In the context of the present invention, the term "oligomeric compound" refers to a polymer having at least a region that is capable of hybridizing to a nucleic acid molecule. The term "oligomeric compound" includes oligonucleotides, oligonucleotide analogs and oligonucleosides as well as nucleotide mimetics and/or mixed polymers comprising nucleic acid and non-nucleic acid components. Oligomeric compounds are routinely prepared linearly but can be joined or otherwise prepared to be circular and may also include branching. Oligomeric compounds can form double stranded constructs such as for example two strands hybridized to form double stranded compositions. The double stranded compositions can be linked or separate and can include overhangs on the ends. In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The term "nucleobase" or "heterocyclic base moiety" as used herein, is intended to by synonymous with "nucleic acid base or mimetic thereof." In general, a nucleobase is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C\equiv C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Oligomeric compounds of the present invention may also contain one or more nucleosides having modified sugar moieties. The furanosyl sugar ring can be modified in a number of ways including substitution with a substituent group, bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920, 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ substituent group; 4'-thio modified sugars and bicyclic modified sugars.

As used herein the term "nucleoside mimetic" is intended to include those structures used to replace the sugar or the sugar and the base not the linkage at one or more positions of an oligomeric compound such as for example nucleoside mimetics having morpholino or bicyclo[3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage.

The oligomeric compounds in accordance with the present invention can comprise from about 8 to about 80 nucleosides and/or modified nucleosides or mimetics in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides and/or modified nucleosides or mimetics in length, or any range therewithin.

In another embodiment, the oligomeric compounds of the invention are 8 to 40 nucleosides and/or modified nucleosides or mimetics in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleosides and/or modified nucleosides or mimetics in length, or any range therewithin.

In another embodiment, the oligomeric compounds of the invention are 8 to 20 nucleosides and/or modified nucleosides or mimetics in length. One having ordinary skill in the art will appreciate that this embodies oligomeric compounds of 8, 9, 10, 11, 12, 13, 14, 15, 16, 17, 18, 19 or 20 nucleosides and/or modified nucleosides or mimetics in length, or any range therewithin.

In another embodiment, the oligomeric compounds of the invention are 10 to 16 nucleosides and/or modified nucleosides or mimetics in length. One having ordinary skill in the art will appreciate that this embodies oligomeric compounds of 10, 11, 12, 13, 14, 15 or 16 nucleosides and/or modified nucleosides or mimetics in length, or any range therewithin.

In another embodiment, the oligomeric compounds of the invention are 10 to 14 nucleosides and/or modified nucleosides or mimetics in length. One having ordinary skill in the art will appreciate that this embodies oligomeric compounds of 10, 11, 12, 13 or 14 nucleosides and/or modified nucleosides or mimetics in length, or any range therewithin.

Chimeric oligomeric compounds have differentially modified nucleosides at two or more positions and are generally defined as having a motif. Chimeric oligomeric compounds of the invention may be formed as composite structures of two or more oligonucleotides, oligonucleotide analogs, oligonucleosides and/or oligonucleotide mimetics as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Oligomerization of modified and unmodified nucleosides and mimetics thereof, in one aspect, is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The oligomeric compounds can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the oligomeric compounds, either alone or in combination with other oligomeric compounds or therapeutics, can be used as tools in differential and/or combinatorial analyses to elucidate expression patterns of a portion or the entire complement of genes expressed within cells and tissues.

The oligomeric compounds are useful for research and diagnostics, because these oligomeric compounds hybridize to nucleic acids encoding proteins. For example, oligonucleotides that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

EXAMPLES

While the present invention has been described with specificity in accordance with certain of its embodiments, the following examples serve only to illustrate the invention and are not intended to limit the same.

Example 1

Preparation of 3-O-Naphthylmethyl-4-(hydroxymethyl)-1,2-O-isopropylidene-α-D-erythro-pentofuranose (5)

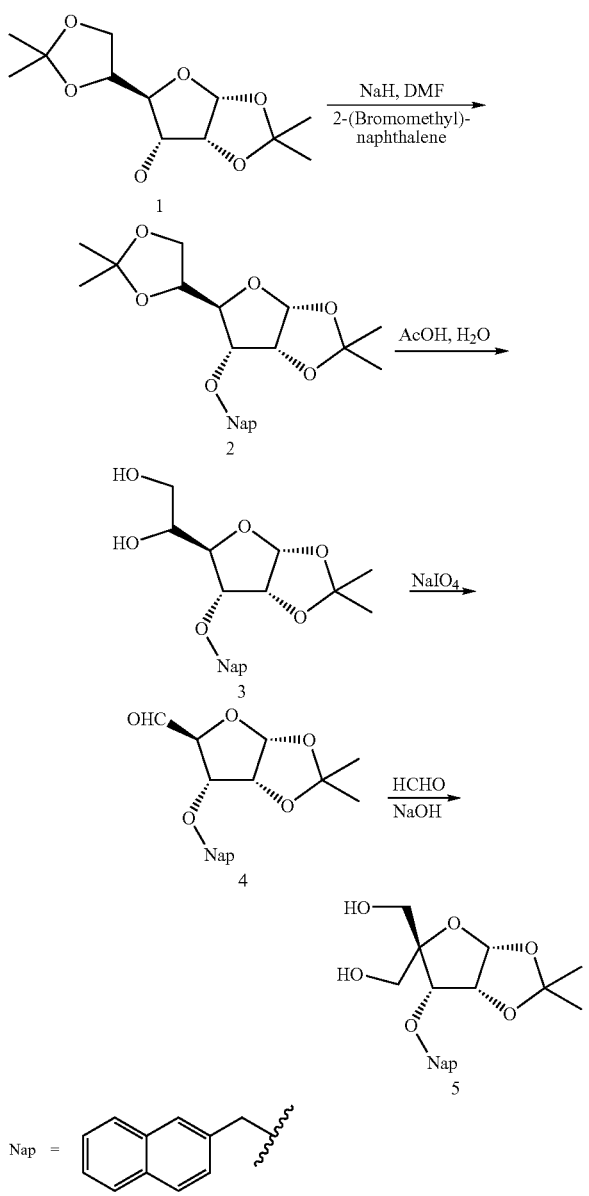

A) Compound 2

Commercially available sugar 1 (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more starting sugar 1. The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide 2 (206.0 g, 99%) as an off-white solid. $^1$H NMR (300 MHz, $CDCl_3$) d: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

B) Compound 3

Compound 2 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of 2. The reaction was then concentrated under reduced pressure until most of the acetic acid was removed. The remaining solution was poured into a stirred mixture of EtOAc (1L) and water (1 L). Solid KOH was then added to the above mixture until the aqueous layer was strongly basic (pH>12). The organic layer was then separated, washed with saturated sodium bicarbonate solution, brine, dried ($Na_2SO_4$), filtered and concentrated under reduced pressure to provide 3 as a yellow foam, which was used without any further purification.

C) Compound 4

A solution of $NaIO_4$ (107.0 g) in water (3 L) was added over 40 minutes to a stirred (mechanical stirrer) solution of compound 3 (crude from Step B, above) in dioxane (1.5 L). After 60 minutes the reaction mixture was poured into EtOAc (1.5 L) and the organic layer was separated, washed with water (1 L), brine (1L), dried ($Na_2SO_4$) and concentrated to provide 4 as a yellow oil, which was used without any further purification.

D) Compound 5

Compound 4 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction and the stirring was continued at room temperature for 3 days. The reaction was then poured into EtOAc (1 L) and washed with water (1 L), brine (1 L) and evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over $P_2O_5$ to provide 5 as a white solid (124 g, 66% from 2). $^1$H NMR (300 MHz, $CDCl_3$) d: 7.85 (m, 4H), 7.48 (m, 3H), 5.75 (d, 1H, J=3.9), 4.96 (d, 1H. J=11.8), 4.75

(d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

Example 2

Protection of 5'-hydroxyl

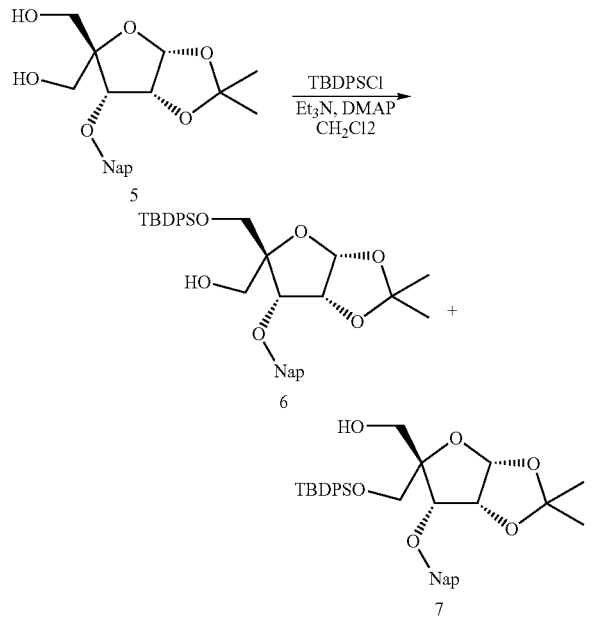

A) Preparation of Compound 6 and 7 tert-Butyldiphenylchlorosilane (305.0 mmol, 84.0 mL) was added to a cold (0° C.) stirring solution of diol 5 (278.0 mmol, 100.0 g) and triethylamine (305 mmol, 43.0 mL) in dichloromethane (600 mL). After the addition was complete, the reaction was warmed to room temperature and the stirring was continued for 16 hours. MeOH (50 mL) was added (to quench the excess TBDPSCl) to the reaction and the stirring was continued for another 2 hours at room temperature. The reaction was then diluted with chloroform and the organic layer was washed with 10% HCl, saturated NaHCO$_3$, brine, dried (Na$_2$SO$_4$) and concentrated to provide a thick oil. Hexanes (150 mL) was added to the oil and the mixture was sonicated until a solution resulted. The solution was now seeded with a small amount of 6 (previously isolated by column chromatography). After standing for 16 hours additional hexanes was added to the thick slurry and the solid was collected by filtration. The solid was then resuspended in hexanes and stirred vigorously for 30 minutes. The solid was collected by filtration to provide 6 (80.5, 48% g) after drying under high vacuum for 16 hours. The filtrates were combined and concentrated under reduced pressure. The resulting oil was redissolved in minimum amount of hexanes and passed through a plug of silia gel (eluting with 20% EtOAc in hexanes). Fractions containing the product 6 were combined, concentrated and crystallized as described above to provide a second crop of 6 (20 g, 12%) as a white solid. Further elution of the silica gel plug with 50% EtOAc in hexanes provided pure 7 (40.0 g, 24%) as a thick oil. In addition a mixture of 6 and 7 (ca 15 g, 9%) was also isolated as a thick oil. Diol 6; $^1$H NMR (300 MHz, CDCl$_3$) δ: 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H). Diol 7; $^1$H NMR (300 MHz, CDCl$_3$) δ: 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

B) Recovery of Compound 5 from Compound 7

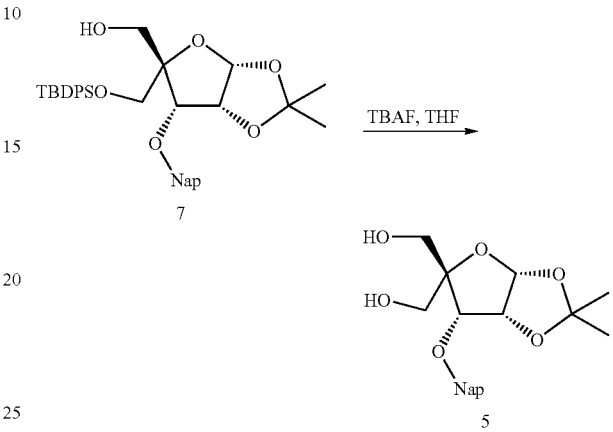

Tetrabutylammonium fluoride (70 mL of a 1M solution in THF) was added to a cold (0° C.) stirring solution of Compound 7 (62.7 mmol, 37.5 g) in THF (250 mL) after which, the reaction was allowed to warm to room temperature gradually. After stirring for an additional 72 hours, the reaction was concentrated under vacuum and the residue was poured onto crushed ice. The flask was rinsed with THF (3 times) and the rinse THF was added to the above suspension. The supernatent was removed by decantation and the solid at the bottom was added to a stirring mixture of hexanes (200 mL) and water (200 mL). After stirring for 2 hours, the resultant flocculent solid was collected by filtration, washed with additional water and hexanes and dried under high vacuum to provide Compound 5 (20 g, 89%) as a white solid.

Example 3

General Procedures for the Preparation of 4'-CH$_2$—O-2' Bridged Bicyclic Nucleosides (Compound 15, DMT, Phosphoramidite)

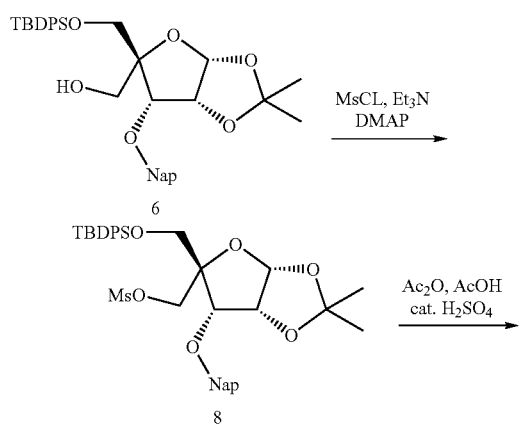

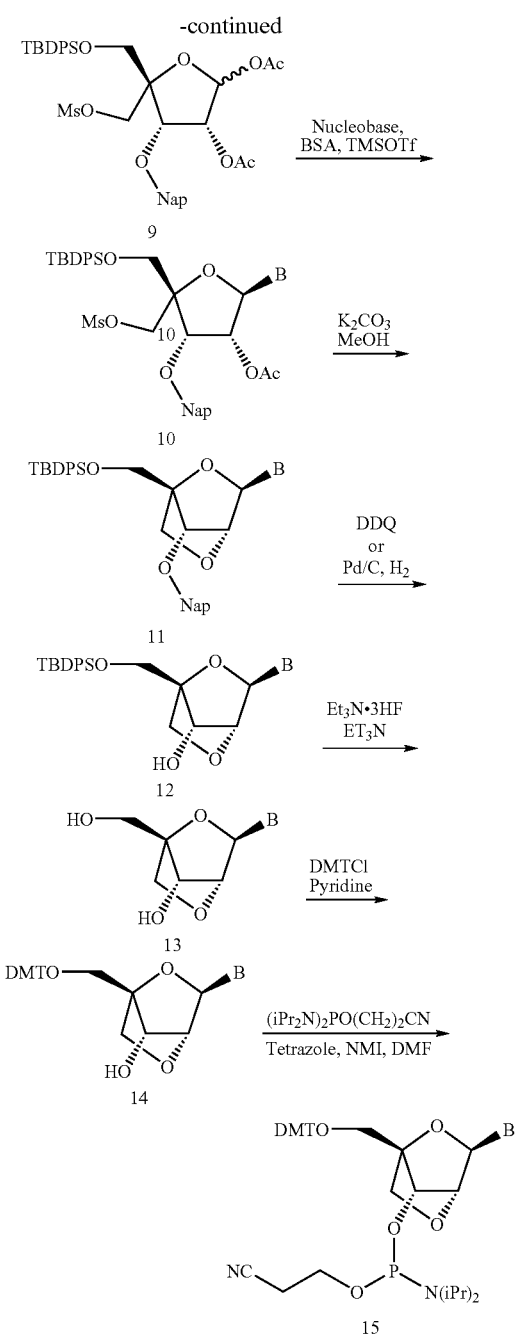

A) 1,2-O-isopropylidene-3-β-napthylmethyl-5-O-tertbutyldiphenylsilyl-4-C-mesyloxymethyl Ribose (8)

Methanesulfonyl chloride (68.2 mmol, 5.28 mL) was added dropwise to a stirring solution of alcohol 6 (42.6 mmol, 25.5 g) in a mixture of anhydrous $CH_2Cl_2$ (200 mL) and anhydrous pyridine (150 mL). After stirring at room temperature for 2 hours, the mixture was concentrated in vacuo. This residue was resuspended in EtOAc, washed with saturated aq. $NaHCO_3$, dried over anhydrous $Na_2SO_4$, filtered, concentrated, and vacuum dried to 28.8 g (99%) of 8 as a sticky pale foam.

B) 1,2-bis-α-acetyl-3-β-napthylmethyl-5-O-tertbutyldiphenylsilyl-4-C-mesyloxymethyl Ribose (9)

Compound 8 (28.8 g, 42.6 mmol) was dissolved in a mixture of glacial acetic acid (125 mL) and acetic anhydride (30 mL). To this mixture was added conc. $H_2SO_4$ (8 drops). After stirring for 2 hours at room temperature, the mixture was concentrated in vacuo to 20 mL and redissolved in EtOAc (500 mL). Washed carefully with saturated aq. $NaHCO_3$ to neutralize (until pH ~6), dried over anhydrous $Na_2SO_4$, filtered, evaporated, and dried to yield 30.2 g (98%) of 9 as a pale oil.

C) 2'-O-acetyl-3'-O-napthylmethyl-5'-O-tertbutyldiphenylsilyl-4'-C-methanesulfonyloxymethyl Uridine (10)

N,O-Bis(trimethylsilyl)acetamide (47.8 mL, 195 mmol) was added to a suspension of Compound 9 (30.0 g, 41.6 mmol) and uracil (7.0 g, 62.4 mmol) in anhydrous $CH_3CN$ (236 mL). Mixture was heated at 55° C. for 1.5 hours until all solids had dissolved. Cooled solution to 0° C., then added trimethylsilyl triflate (15.0 mL, 83.2 mmol). After 15 minutes the solution was heated to 55° C. for 5.5 hours. The mixture was subsequently cooled back to 0° C., treated dropwise with saturated aqueous $NaHCO_3$ until a white precipitate persisted, concentrated in vacuo to a white paste, then resuspended in EtOAc. Washed with aq. $NaHCO_3$, dried over anhydrous $Na_2SO_4$, filtered, evaporated, and dried in vacuo to 30.8 g (96%) of 10 as a pale yellow foam.

D) 3'-O-napthylmethyl-5'-O-tertbutyldiphenylsilyl-2'-O,4'-C-methylene Uridine (11)

Solid $K_2CO_3$ (11.1 g, 80 mmol) was added to a solution of compound 10 (29.4 g, 38 mmol) in methanol (350 mL). After stirring at room temperature for 5 hours, mixture was poured into EtOAc, washed with aqueous $NaHCO_3$, dried over anhydrous $Na_2SO_4$, filtered, and concentrated in vacuo to a yellow foam. Purification by silica gel chromatography (1% methanol in $CH_2Cl_2$) yielded 20.0 g (83%) of nucleoside 11 as a pale yellow foam.

E) 5'-O-tertbutyldiphenylsilyl-2'-O,4'-C-methylene Uridine (12)

2,3-Dichloro-5,6-dicyano-1,4-benzoquinone (15.9 g, 70.0 mmol) was added to a mixture of compound 11 (19.7 g, 31.1 mmol) in $CH_2Cl_2$ (200 mL) and $H_2O$ (40 mL). After 7 hours of vigorous stirring at room temperature, the mixture was poured into $CH_2Cl_2$ (1 L). The resulting solution was washed with 2% (w/v) aqueous sodium bisulfite, followed by saturated aqueous $NaHCO_3$, then dried over anhydrous $Na_2SO_4$, filtered, then evaporated to a light-brown foam. Purification by silica gel chromatography (2.5 vol. % methanol in $CH_2Cl_2$) yielded 15.0 g (97%) of 12 as an off-white foam.

F) 2'-O,4'-C-methylene Uridine (13)

Compound 12 (13.2 g, 26.7 mmol) was dissolved in anhydrous THF (60 mL). To this mixture was added tetrabutylammonium fluoride (TBAF, 29.4 mmol, 29.4 mL of a 1 M solution in THF). After stirring at room temperature for 2 hours, mixture was concentrated in vacuo to ~15 mL and then eluted through a short silica gel column with 10% methanol in $CH_2Cl_2$. Eluate was concentrated to a pale solid, which was washed on a glass frit with a minimal amount of ice-cold methanol. The remaining solid was dried in vacuo to yield 5.78 g (84%) of 13 as a white solid.

G) 5'-O-(4,4'-dimethoxy)trityl-2'-O,4'-C-methylene Uridine (14)

To a solution of compound 13 (2.10 g, 8.2 mmol) in anhydrous pyridine (30 mL) was added dimethylaminopyridine (DMAP, 150 mg, 1.23 mmol) and 4,4'-dimethoxytrityl chloride (4.17 g, 12.3 mmol). After stirring at room temperature for 3 hours the mixture was concentrated in vacuo to a dark oil, redissolved in $CH_2Cl_2$ (250 mL), washed with aqueous $NaHCO_3$, dried over anhydrous $Na_2SO_4$, filtered, then concentrated in vacuo to a dark yellow oil. Silica gel chromatography (elution with 1.5% methanol in $CH_2Cl_2$) yielded 4.50 g (98%) of 14 as an off-white foam.

H) 5'-O-(4,4'-dimethoxy)trityl-2'-O,4'-C-methylene Uridine 3'-O-(2-cyanoethyl)-N,N-diisopropylamino-phosphoramidite (15)

To a solution of compound 14 (6.42 g, 11.5 mmol) in $CH_2Cl_2$ was added N,N-diisopropylethylamine (10.0 mL, 57.5 mmol), followed by 2-cyanoethyl-N,N-diisopropylamino-chlorophosphoramidite (5.1 mL, 23.0 mmol). After stirring at room temperature for 3 hours the mixture was poured into EtOAc (400 mL), washed with aqueous $NaHCO_3$, dried over anhydrous $Na_2SO_4$, filtered, and evaporated to a pale oil. Silica gel chromatography yielded 7.4 g (84%) of 15 as an off-white foam.

Example 4

General Procedures for the Preparation of 4'-(CH$_2$)$_2$—O-2' Bridged Bicyclic Nucleosides (Compound 26, DMT, Phosphoramidite)

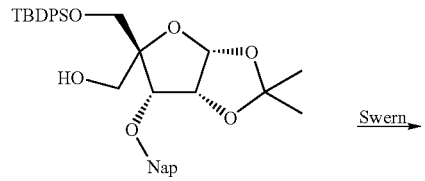
6    Swern→

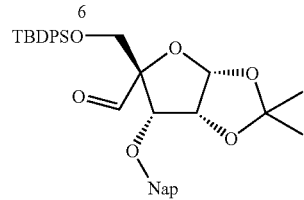
16    Wittig→

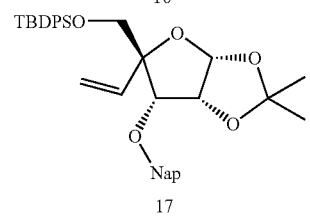
17    9-BBN, H$_2$O$_2$→

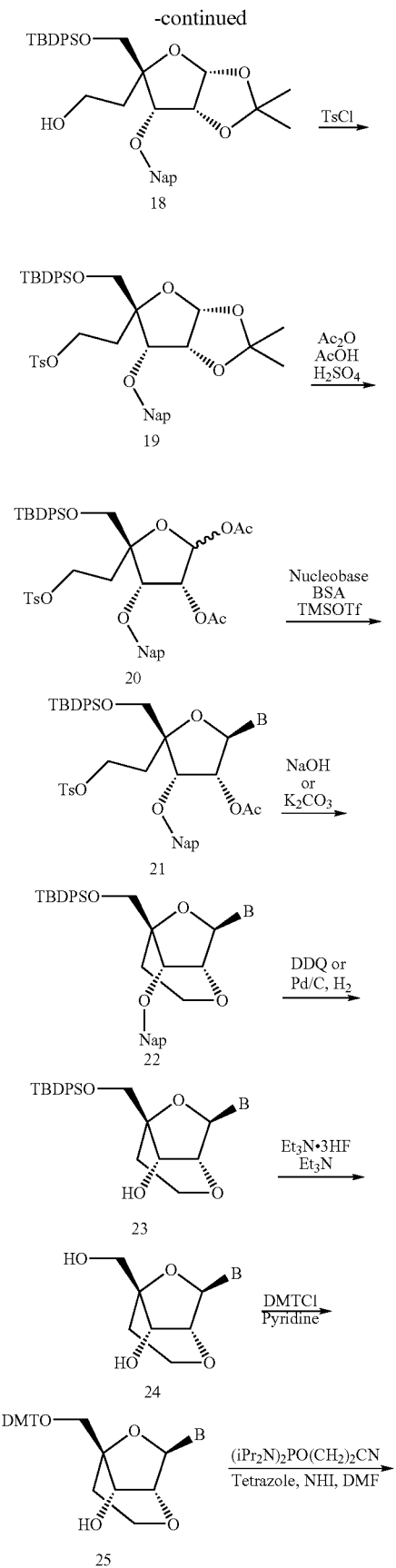

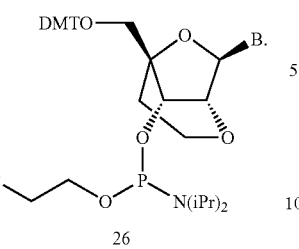
Example 5
Preparation of uridine-6-(S)-methyl BNA Phosphoramidite, (1S,3R,4R,6S,7S)-7-[2-cyanoethoxy(diisopropylamino)phosphin oxy]-1-(4,4'-dimethoxytrityloxymethyl)-3-(uracil-1-yl)-6-methyl-2,5-dioxa-bicyclo[2.2.1]heptane (Compound 37)
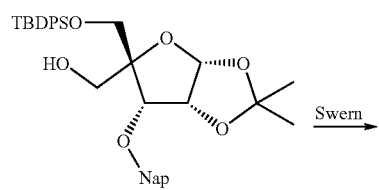
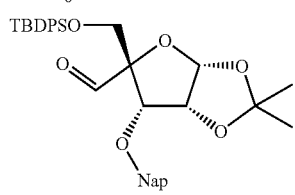
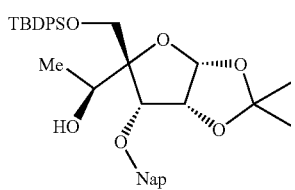
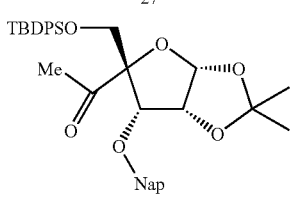
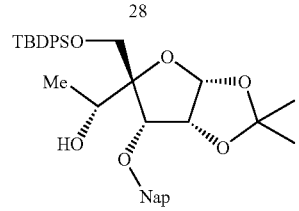
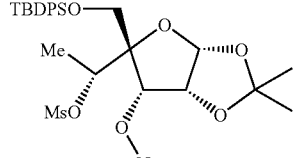
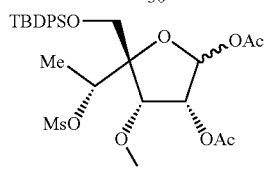
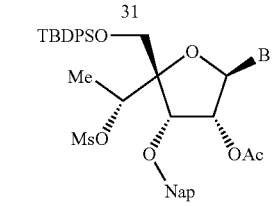
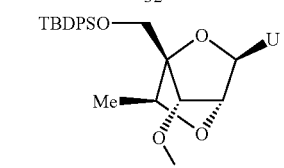
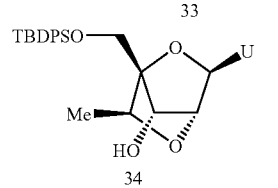
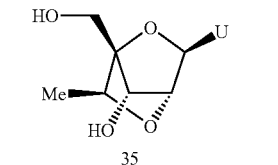
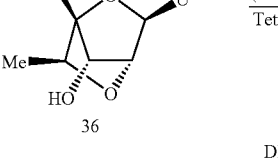
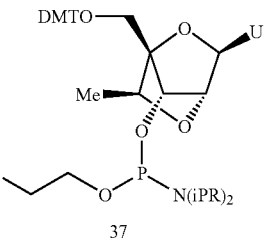
A) Alcohol (27)
Dimethylsulfoxide (1.6 mL, 22.4 mmol) was added dropwise to a cold (−78° C.) solution of oxalyl chloride (0.98 mL, 11.2 mmol) in CH$_2$Cl$_2$ (70 mL). After stirring for 30 min, a solution of Compound 6 (Example 2, 4.8 g, 8.0 mmol) in CH$_2$Cl$_2$ (20 mL) was added to the reaction. The stirring was continued for 45 minutes at –78° C. and triethylamine (4.72 mL, 33.7 mmol) was added to the reaction. The reaction was stirred at –78° C. for 15 minutes after which the ice bath was removed and the reaction was allowed to gradually warm over 45 minutes. The reaction was then poured into CH$_2$Cl$_2$ and the organic phase was sequentially washed with 5% aqueous HCl, saturated NaHCO$_3$, brine, dried (Na$_2$SO$_4$) and concentrated under vacuum to provide Compound 16, which was used without any further purification.

A suspension of cerium III chloride (2.96 g, 12.0 mmol) in THF (50 mL) was stirred at room temperature for 90 minutes. The reaction was cooled in an ice bath and methyl magnesium bromide (8.6 mL of a 1.4 M solution in THF, 12 mmol) was added over 5 minutes and the stirring continued for another 90 minutes after which the reaction was cooled to –78° C. A solution of crude Compound 16 (from above) in THF (20 mL) was added to the reaction. After stirring for another 90 min, the reaction was quenched with sat NH$_4$Cl solution and poured into EtOAc. The organic layer was sequentially washed with 5% aqueous HCl, saturated NaHCO$_3$, brine, dried (Na$_2$SO$_4$) and concentrated under vacuum. Purification by column chromatography (SiO$_2$, eluting with 20% EtOAc/hexanes) provided Compound 27 (4.37 g, 89% from Compound 6).

B) Diacetate (31)

Dimethylsulfoxide (1.41 mL, 19.9 mmol) was added dropwise to a cold (–78° C.) solution of oxalyl chloride (0.87 mL, 10.0 mmol) in CH$_2$Cl$_2$ (70 mL). After stirring for 30 min, a solution of Compound 27 (4.35 g, 7.1 mmol) in CH$_2$Cl$_2$ (20 mL) was added to the reaction. The stirring was continued for 45 minutes at –78° C. and triethylamine (4.20 mL, 30.0 mmol) was added to the reaction. The reaction was stirred at –78° C. for 15 minutes after which the ice bath was removed and the reaction was allowed to gradually warm over 45 minutes. The reaction was then poured into CH$_2$Cl$_2$ and the organic phase was sequentially washed with 5% aqueous HCl, saturated NaHCO$_3$, brine, dried (Na$_2$SO$_4$) and concentrated under vacuum to provide Compound 28, which was used without further purification.

Diisobutyl aluminum hydride (13.7 mL of a 1M solution in CH$_2$Cl$_2$, 13.7 mmol) was added to a cold solution of Compound 28 (from above) in CH$_2$Cl$_2$ (15 mL). After stirring for 2 hours at –78° C., the reaction was quenched by the addition of saturated NH$_4$Cl and poured into CHCl$_3$. The organic layer was then sequentially washed with 5% aqueous HCl, saturated NaHCO$_3$, brine, dried (Na$_2$SO$_4$) and concentrated under vacuum to provide Compound 29 which was used without further purification.

Methanesulfonyl chloride (0.11 mL, 1.4 mmol) was added to a cold (0° C.) solution of Compound 29 (from above), triethylamine (1.77 mL, 10.5 mmol) and 4-dimethylaminopyridine (85 mg, 0.7 mmol) in CH$_2$Cl$_2$ (21 mL). After stirring at room temperature for 1 hour, the reaction was poured into CHCl$_3$ and the organic layer was sequentially washed with 5% aqueous HCl, saturated NaHCO$_3$, brine, dried (Na$_2$SO$_4$) and concentrated under vacuum to provide Compound 30, which was used without purification.

Concentrated H$_2$SO$_4$ (2 drops) was added to a solution of Compound 30 (from above) in glacial acetic acid (15 mL) and acetic anhydride (3.0 mL). After stirring at room temperature for 1 hour, the reaction was poured into EtOAc and the organic layer was washed with water, saturated NaHCO$_3$, brine, dried (Na$_2$SO$_4$) and concentrated under vacuum. Purification by column chromatography (SiO$_2$, eluting with 20% to 33% EtOAc/hexanes) provided Compound 31 (3.0 g, 58% from Compound 27).

C) Nucleoside (33)

N,O-Bis(trimethylsilyl)acetamide (3.45 mL, 14.0 mmol) was added to a suspension of Compound 31 (3.0 g, 4.1 mmol) and uracil (0.57 g, 5.1 mmol) in CH$_3$CN (20 mL). After heating at 40° C. for 15 minutes to get a clear solution, trimethylsilyl triflate (0.95 mL, 5.3 mmol) was added to the reaction. After refluxing for 2 hours, the reaction was cooled to room temperature and poured into EtOAc. The organic layer was washed with saturated NaHCO$_3$, brine, dried (Na$_2$SO$_4$) and concentrated under vacuum to provide crude nucleoside, Compound 32, which was used without purification.

K$_2$CO$_3$ (1.66 g, 12.0 mmol) was added to a solution of Compound 32 (from above) in MeOH (40 mL). After stirring at room temperature for 16 hours, the reaction was concentrated under vacuum and the residue was dissolved in 25% pyridine/EtOAc and extracted with brine, dried (Na$_2$SO$_4$) and concentrated under vacuum. Purification by column chromatography (SiO$_2$, eluting with 40% EtOAc/hexanes) provided Compound 33 (2.0 g, 76% from Compound 31) as a white solid.

D) Nucleoside (34)

2,3-Dichloro-5,6-dicyano-1,4-benzoquinone (DDQ) (1.4 g, 6.2 mmol) was added to a solution of Compound 33 (2.0 g, 3.1 mmol) in dichloromethane (30 mL) and H$_2$O (1.5 mL). After stirring for 3 hours at room temperature, additional DDQ (0.5 g) was added to the reaction. After stirring for another 10 minutes, the reaction was concentrated under vacuum and the residue was dissolved in EtOAc. The organic layer was then sequentially washed with water, water:saturated NaHCO$_3$ (1:1), brine, dried (Na$_2$SO$_4$) and concentrated. Purification by column chromatography (SiO$_2$, 80% EtOAc/hexanes) provided Compound 34 (1.25 g, 80%) as a white solid.

E) Nucleoside (35)

Triethylamine trihydroflouride (2.4 mL, 14.7 mmol) was added to a solution of Compound 34 (1.25 g, 2.5 mmol) and triethlyamine (1.0 mL, 7.4 mmol) in THF (25 mL) in a polypropylene tube. After stirring at room temperature for 24 hours, the reaction was concentrated under vacuum and the residue was dissolved in EtOAc. The organic layer was then washed with water, saturated NaHCO$_3$, brine, dried and concentrated (Na$_2$SO$_4$). Purification by column chromatography (SiO$_2$, eluting with 5% to 10% MeOH/CHCl$_3$) provided Compound 35 (0.88 g) as a white solid (product contaminated with Et$_3$N).

F) Nucleoside (36)

Dimethoxytrityl chloride (0.91 g, 2.7 mmol) was added to a solution of Compound 35 (from above) in pyridine (12 mL). After stirring at room temperature for 16 hours, the reaction was poured into EtOAc and the organic layer was washed with brine, dried and concentrated. Purification by column chromatography (SiO$_2$, eluting with 90% EtOAc/hexanes) provided Compound 36 (1.28 g, 86% from Compound 35) as a white solid.

G) (1S,3R,4R,6S,7S)-7-[2-Cyanoethoxy(diisopropylamino) phosphin oxy]-1-(4,4'-dimethoxytrityloxymethyl)-3-(uracil-1-yl)-6-methyl-2,5-dioxa-bicyclo[2.2.1]heptane (37)

2-Cyanoethyl tetraisopropylphorodiamidite (0.46 mL, 1.5 mmol) was added to a solution of Compound 36 (0.59 g, 1.0 mmol), tetrazole (57 mg, 0.82 mmol) and N-methylimidazole (20 μL, 0.25 mmol) in DMF (5 mL). After stirring at room temperature for 8 hours, the reaction was poured into EtOAc and the organic layer was washed with 90% brine, brine, dried (Na$_2$SO$_4$) and concentrated. Purification by column chromatography (SiO$_2$, eluting with 66% to 75% EtOAc/hexanes) provided phosphoramidite, Compound 37 as a white solid (0.75 g, 97%). $^{31}$P NMR (CDCl$_3$) δ: 149.36, 149.53.

Example 6

General Procedures for the Preparation of N-isobutyrylguanine-6-(S)-methyl BNA Phosphoramidite, (1S,3R,4R,6S,7S)-7-[2-cyanoethoxy(disopropylamino)phosphin oxy]-1-(4,4'-dimethoxytrityloxymethyl)-3-(2-N-Isobutyrylguanin-9-yl)-6-methyl-2,5-dioxa-bicyclo[2.2.1]heptane (Compound 43)

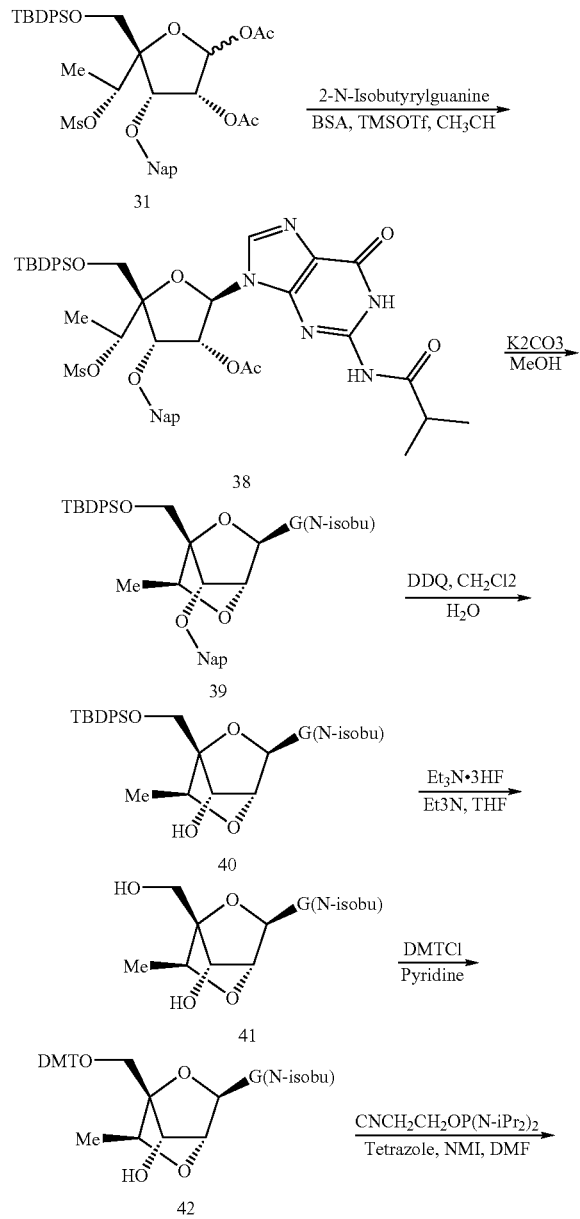

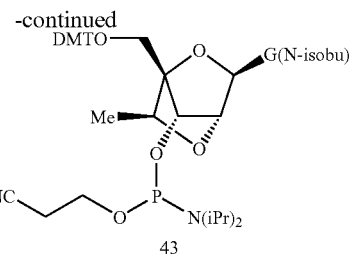

Compound 38 is prepared by the Vorbruggen reaction of Compound 31, 2-N-isobutyrylguanine, BSA and TMSOTf in refluxing CH$_3$CN. The phosphoramidite, Compound 43, is prepared from Compound 38 using the same sequence as that described for the preparation of phosphoramidite, Compound 37, from Compound 31.

Example 7

General Procedures for the Preparation of Uridine BNA Phosphoramidite, (1R,5R,7R,8S)-8-[2-cyanoethoxy(diisopropylamino)phosphin oxy]-5-(4,4'-dimethoxytrityloxymethyl)-7-(uridin-1-yl)-3-methyl-2,6-dioxa-3-aza-bicyclo[3.2.1]octane (Compound 57)

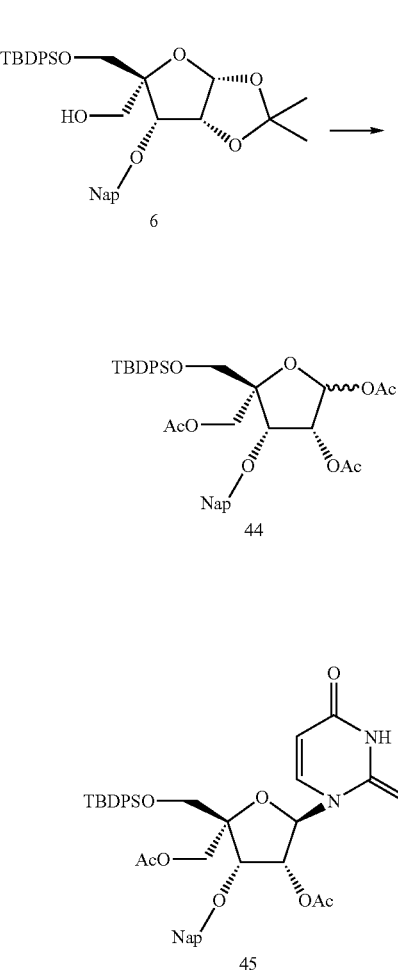

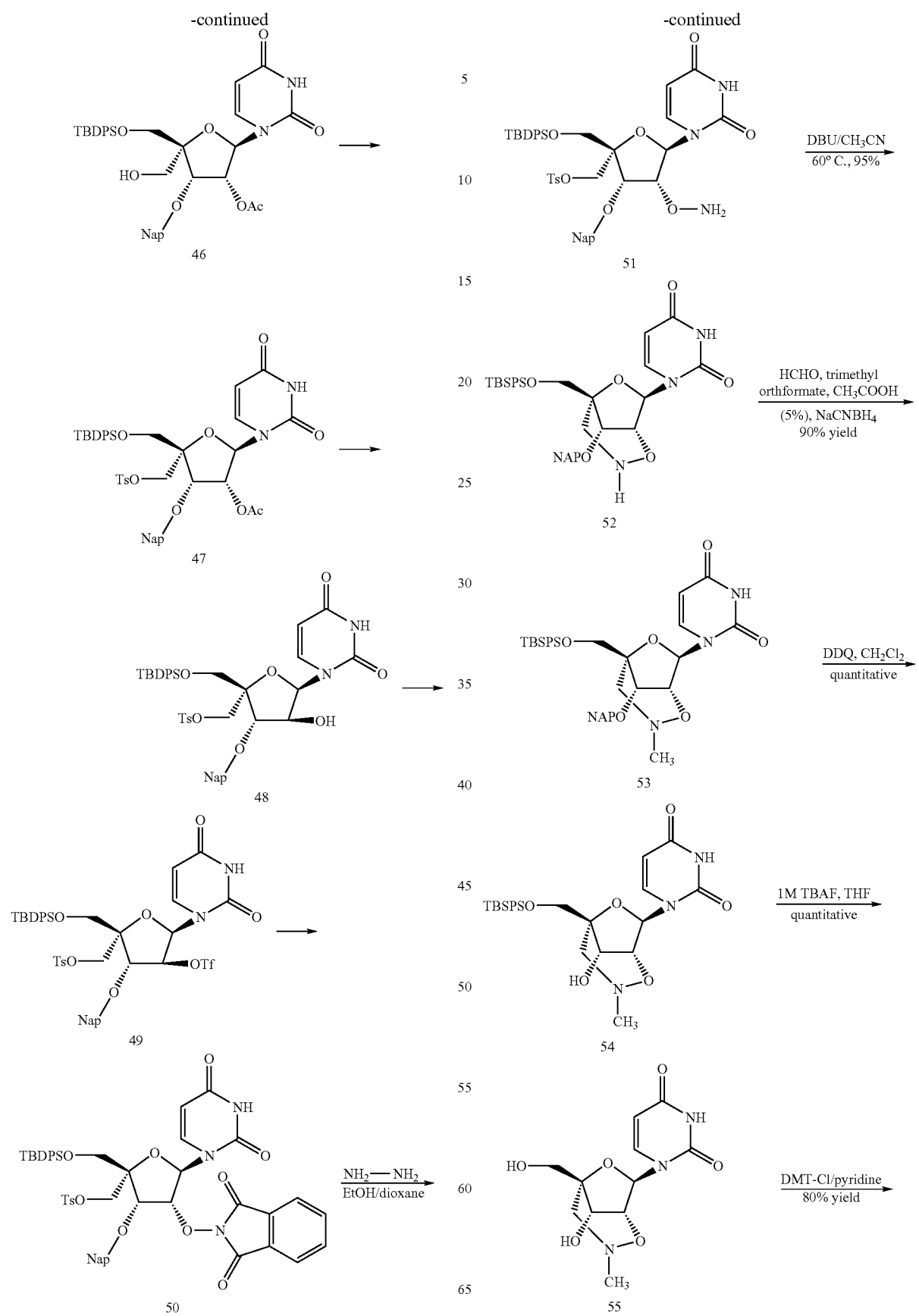

-continued

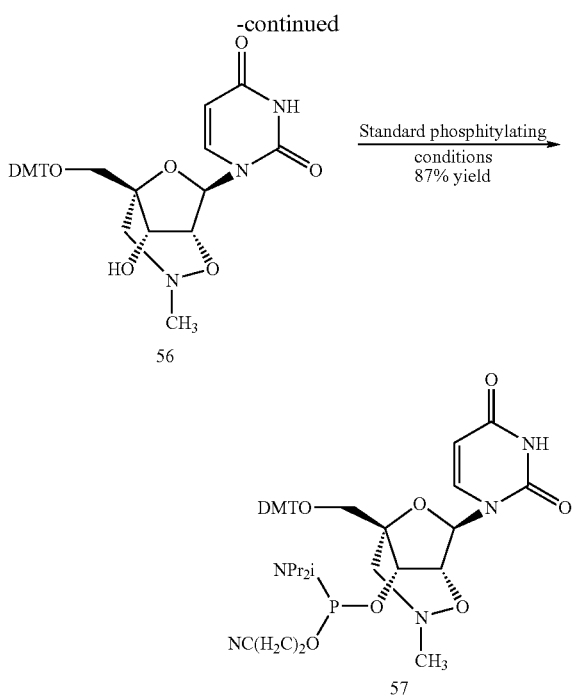

A) 4-C-acetoxymethyl-1,2-bis-O-acetyl-5-O-tert-butyldiphenylsilyl-3-O-naphthylmethylribose (44)

Dried Compound 6 (29.52 g, 49.30 mmol) was dissolved in a mixture of glacial acetic acid (150 mL) and acetic anhydride (37 mL). To this solution was added several drops of concentrated $H_2SO_4$. After 1.5 hours, the resulting light brown solution was diluted in EtOAc (1 L), washed with sat. $NaHCO_3$ (5×1 L), dried over anhydrous $Na_2SO_4$, filtered, evaporated, and dried under high vacuum to yield Compound 44 (33.7 g, 99%) as a pale oil.

B) 2'-O-acetyl-4'-C-acetoxymethyl-5'-O-tertbutyl-diphenylsilyl-3'-O-naphthylmethyluridine (45)

A mixture of Compound 44 (33.24 g, 48.54 mmol) and uracil (8.16 g, 72.81 mmol) was suspended in anhydrous $CH_3CN$ (275 mL). To this mixture was added N,O-bis-trimethylsilylacetamide (55.8 mL, 228 mmol), followed by heating at 55° C. for 1 hour. The mixture was cooled to 0° C. then trimethylsilyl trifluoromethanesulfonate (17.5 mL, 97.1 mmol) was added dropwise over 15 minutes. The mixture was subsequently heated at 55° C. After 3 hours, the mixture was cooled to 0° C., quenched with the dropwise addition of saturated aqueous $NaHCO_3$. The mixture was poured into EtOAc, washed with brine (4×0.8 mL), dried over anhydrous $Na_2SO_4$, filtered, evaporated, and dried under high vacuum to yield Compound 45 (35.6 g, 99%) as a pale yellow foam.

C) 5'-O-tertbutyldiphenylsilyl-4'-C-hydroxymethyl-3'-O-naphthylmethyluridine (46)

To a solution of Compound 45 (34.9 g, 47.08 mmol) in anhydrous methanol (250 mL) was added tertbutylamine (26.3 mL, 250 mmol). After stirring at room temperature for 24 hours, the mixture was concentrated in vacuo, redissolved in EtOAc (0.8 L), washed with saturated aqueous $NaHCO_3$, dried over anhydrous $Na_2SO_4$, filtered, evaporated and dried under high vacuum to yield Compound 46 (30.6 g, 99%) as a pale yellow foam.

D) 5'-O-tertbutyldiphenylsilyl-3'-O-naphthylmethyl-2'-O-toluenesulfonyl-4'-C-toluenesulfonyloxymethy-luridine (47)

Dried Compound 46 (29.24 g, 44.79 mmol) was dissolved in a mixture of anhydrous pyridine (82 mL) and anhydrous $CH_2Cl_2$ (82 mL). To this solution was added toluenesulfonyl chloride (21.3 g, 112 mmol). After stirring at room temperature for 10 hours, the mixture was poured into EtOAc (1 L), washed with saturated aqueous $NaHCO_3$ (2×0.8 L), then with 1% (v/v) aqueous AcOH (2×0.8 L). Dried over anhydrous $Na_2SO_4$, filtered, and evaporated to a brown oil. Purification by silica gel chromatography (2:1 hexanes:EtOAc) yielded Compound 47 (32.36 g, 75%) as a pale yellow foam.

E) 5'-O-tertbutyldiphenylsilyl-3'-O-naphthylmethyl-4'-C-toluenesulfonyloxymethyl-2'-arabinouridine (48)

To a solution of Compound 47 (29.6 g, 30.8 mmol) in anhydrous $CH_3CN$ (140 mL) was added 1,8-diazabicyclo[5.4.0]undec-7-ene (6.9 mL, 46.2 mmol). After stirring at room temperature for 1.5 hours, the mixture was diluted with EtOAc (1 L), washed 1% (v/v) aq. AcOH (1×0.8 L) and brine (2×0.8 L), dried over anhydrous $Na_2SO_4$, filtered, and evaporated to a pale orange foam. The foam was redissolved in 1,4-dioxane (250 mL) and 2 M aq. NaOH (55 mL) was added. After 45 minutes, the mixture was neutralized with AcOH, diluted in EtOAc (1 L), washed with saturated aqueous $NaHCO_3$ (1×0.8 L) and brine (2×0.8 L), dried over anhydrous $Na_2SO_4$, filtered, and evaporated to a pale foam. Purification by silica gel chromatography (1:1 hexanes:EtOAc) yielded Compound 48 (19.28 g, 78%-2 steps) as an off-white foam.

F) 5'-O-tertbutyldiphenylsilyl-3'-O-naphthylmethyl-4'-C-toluenesulfonyloxymethyl-2'-O-trifluo-romethanesulfonyl Arabinouridine (49)

To a solution of compound 48 (19.5 g, 24.2 mmol) in $CH_2Cl_2$ (98 mL) was added N,N-dimethylaminopyridine (11.8, 97 mmol). Solution was cooled to −10° C. with an ice/ethanol bath. To the chilled solution was added trifluoromethanesulfonic anhydride (6.11 mL, 36.4 mmol) as a solution in $CH_2Cl_2$ (28 mL). After stirring at −10° C. for 1.5 hours, mixture was diluted with 500 mL of EtOAc. Washed with ice-cold saturated aqueous $NaHCO_3$ (2×500 mL). The mixture was dried over anhydrous $Na_2SO_4$, filtered, and evaporated to an orange foam. Purification by silica gel chromatography (1:1 hexanes:EtOAc) yielded 13.2 g (58%) of compound 49 as an off-white foam.

G) 5'-O-tertbutyldiphenylsilyl-3'-O-naphthylmethyl-4'-C-toluenesulfonyloxymethyl-2'-O-phthalimido Uridine (50)

To a solution of Compound 49 (16.3 g, 17.4 mmol) in anhydrous $CH_3CN$ (151 mL) was added N-hydroxyphthalimide (4.54 g, 27.8 mmol), followed by 1,8-diazabicyclo[5.4.0]undec-7-ene (4.1 mL, 27.8 mmol). After stirring at room temperature for 2 hours, the mixture was concentrated in vacuo to 75 mL, then diluted with EtOAc (500 mL), washed with 1% (v/v) aq. AcOH and saturated aqueous NaHCO$_3$, dried over anhydrous Na$_2$SO$_4$, filtered, and evaporated to yield Compound 50 (15.3 g, 89%) as a pale foam.

H) 2'-O-amino-5'-O-tertbutyldiphenylsilyl-3'-O-naphthylmethyl-4'-C-toluenesulfonyloxymethyl Uridine (51)

To a solution of Compound 50 (15.9 g, 16.7 mmol) in anhydrous EtOH (500 mL) is added hydrazine hydrate (1.46 mL, 30.1 mmol). After stirring at room temperature for 3 hours, the mixture is concentrated in vacuo to ~100 mL, then poured into EtOAc (500 mL) and washed with saturated aqueous NaHCO$_3$ (2×100 mL). The organic phase is dried over anhydrous Na$_2$SO$_4$, filtered and evaporated. The crude Compound 51 is used without further purification I) 1-[5-(tert-Butyl-diphenyl-silanyloxymethyl)-8-(naphthalen-2-ylmethoxy)-2,6-dioxa-3-aza-bicyclo[3.2.1]oct-7-yl]-1H-pyrimidine-2,4-dione (52)

To a solution of crude 51 (13.1 g, 16.0 mmol) in anhydrous CH$_3$CN (150 mL) was added 1,8-diazabicyclo[5.4.0]undec-7-ene (9.55 mL, 63.9 mmol). This solution was heated at 60° C. for 6 hours. The mixture was cooled to room temperature, concentrated in vacuo to ~50 mL, diluted with EtOAc (500 mL). Washed with aqueous NaHCO$_3$, dried over anhydrous Na$_2$SO$_4$, filtered then evaporated to a pale orange foam. Silica gel chromatography (2% methanol in CH$_2$Cl$_2$) yielded 10.1 g (97%) of 52 as a pale yellow foam.

J) 1-[5-(tert-Butyl-diphenyl-silanyloxymethyl)-3-methyl-8-(naphthalen-2-ylmethoxy)-2,6-dioxa-3-aza-bicyclo[3.2.1]oct-7-yl]-1H-pyrimidine-2,4-dione (53)

To a solution of compound 52 (1 mmol) in CH$_3$COOH (5 mL) and trithylortoformate (1 mL), 20% aq. HCHO (0.16 mL, 1.1 mmol) was added at 0° C. After 15 minutes NaBH$_3$CN (2 mmol) is added. After an additional 1 hour the mixture is poured into EtOAc (250 mL), washed with saturated aqueous NaHCO$_3$ (2×250 mL), dried over anhydrous Na$_2$SO$_4$, filtered and evaporated. Purification by silica gel chromatography gave compound 53 in 90% isolated yield.

K) 1-[5-(tert-Butyl-diphenyl-silanyloxymethyl)-8-hydroxy-3-methyl-2,6-dioxa-3-aza-bicyclo[3.2.1]oct-7-yl]-1H-pyrimidine-2,4-dione (54)

To a solution of compound 53 (1 mmol) in anhydrous CH$_2$Cl$_2$ (10 mL) was added water (0.8 mL) and the biphasic solution was stirred for 5 minutes. To this solution is added DDQ (2.2 mmol). The reaction mixture was stirred for 8 hours when the reaction was complete. It was diluted with CH$_2$Cl$_2$ (100 mL) and washed with 2% sodium bisufite solution. The aqueous layer was extracted until all the compound was in organic layer. The organic layer was washed with saturated bicarbonate followed by brine then dried over anhydrous sodium sulfate. The solvent was removed under reduced pressure and the product was purified on silica gel to give compound 54 in nearly quantitative yield.

L) 1-(8-Hydroxy-5-hydroxymethyl-3-methyl-2,6-dioxa-3-aza-bicyclo[3.2.1]oct-7-yl)-1H-pyrimidine-2,4-dione (55)

To a solution of compound 54 (1 mmol) in THF (5 mL) was added TBAF (2.5 mmol, 2.5 mL of a 1 M solution in THF). After stirring at room temperature for 2 hours, mixture was concentrated. Purification of the resultant residue by silica gel chromatography gave compound 55 near quantitative yield M) 1-{5-[Bis-(4-methoxy-phenyl)-phenyl-methoxymethyl]-8-hydroxy-3-methyl-2,6-dioxa-3-aza-bicyclo[3.2.1]oct-7-yl}-1H-pyrimidine-2,4-dione (56)

To a solution of compound 55 (1 mmol) in anhydrous pyridine (4 mL) was added 4,4'-dimethoxytrityl chloride (1.5 mmol). After stirring at room temperature for 6 hours the mixture was quenched with MeOH and then concentrated in vacuo. The residue was dissolved in CH$_2$Cl$_2$ (100 mL), washed with saturated aqueous NaHCO$_3$ (2×20 mL), brine (20 mL) and the organic layer dried over Na$_2$SO$_4$, filtered, and evaporated. The residue was purified by silica gel chromatography. Appropriate fractions were collected, concentrated to give compound 56 in 80% yield.

N) Uridine BNA Phosphoramidite, (1R,5R,7R,8S)-8-[2-cyanoethoxy(diisopropyl-amino)phosphin oxy]-5-(4,4'-dimethoxytrityloxymethyl)-7-(uridin-1-yl)-3-methyl-2,6-dioxa-3-aza-bicyclo[3.2.1]octane (Compound 57)

To a solution of 56 (1 mmol) in anhydrous DMF (3.3 mL) was added N,N,N',N'-tetraisopropylamino-2-cyanoethylphosphoramidite (1.75 mmol) and tetrazole (0.75 mmol). After stirring at room temperature for 15 minutes, N-methylimidazole (0.25 mmol) was added. Stirring was maintained for an additional 6 hours and Et$_3$N (8 mmol) was added. The mixture was then poured into EtOAc (100 mL), washed with saturated aqueous NaHCO$_3$ (2×100 mL), dried over anhydrous Na$_2$SO$_4$, filtered and evaporated. Purification by silica gel chromatography gave the amidite 57 in 87% yield Example 8

General Procedures for the Preparation of Cytidine BNA Phosphoramidite, (1R,5R,7R,8S)-8-[2-cyanoethoxy(diisopropylamino)phosphin oxy]-5-(4,4'-dimethoxytrityloxymethyl)-7-(4-N-benzoyl-cytosin-1-yl)-3-methyl-2,6-dioxa-3-aza-bicyclo [3.2.1]octane (59)

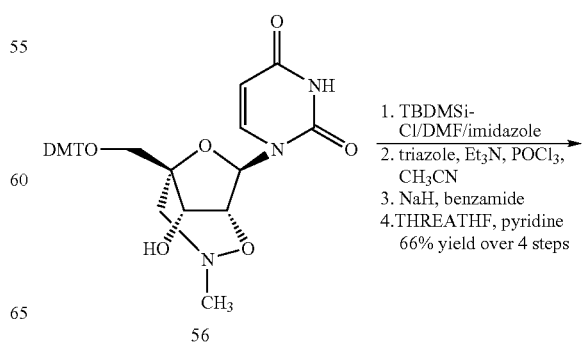

1. TBDMSi-Cl/DMF/imidazole
2. triazole, Et$_3$N, POCl$_3$, CH$_3$CN
3. NaH, benzamide
4. THREATHF, pyridine
66% yield over 4 steps

56

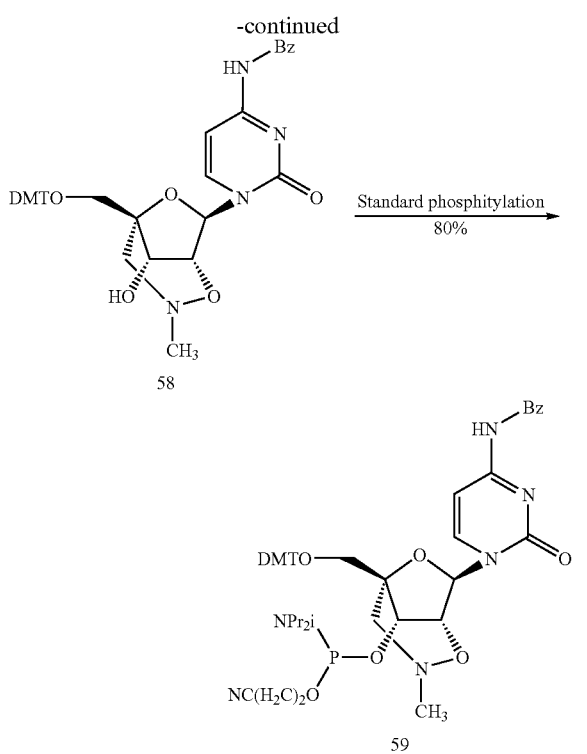

A) 1-{5-[Bis-(4-methoxy-phenyl)-phenyl-methoxymethyl]-hydroxy-3-methyl-2,6-dioxa-3-aza-bicyclo[3.2.1]oct-7-yl]-2-oxo-1,2-dihydro-pyrimidin-4-yl}-benzamide (58)

Vacuum dried imidazole (4.4 mmol) and TBDMSiCl (2.2 mmol) was added to a mixture of compound 56 (1 mmol) dissolved in anhydrous DMF (5 mL). The reaction mixture was stirred for 20 h. The mixture was diluted with ethylacetate (50 mL) and washed with aqueous saturated sodium bicarbonate (2×20 mL) followed by water (2×20 mL). The organic layer was dried over sodium sulfate, concentrated and used without purification for the next step.

To a suspension of 1,2,4-triazole (14 mmol) in $CH_3CN$ (11 mL) at 0° C. was added dropwise $POCl_3$ (4 mmol). The mixture was stirred at 0° C. for 20 minutes after the addition is finished, then anhydrous $Et_3N$ (20 mmol) was added dropwise. To this solution was added the crude material from the previous step (1 mmol) as a solution in $CH_3CN$ (4.4 mL). After stirring at 0° C. for 5 hours, the mixture was poured into saturated aqueous $NaHCO_3$ and extracted with EtOAc (100 mL). The organic layer was dried over anhydrous $Na_2SO_4$, filtered and evaporated. The residue then was dissolved in anhydrous DMF (5 mL) and treated with a NaHCOPh (1.2 mmol, 2.4 mL of a 0.5 M solution in DMF) at 0° C. The mixture was stirred for 2 hours, poured into EtOAc (200 mL), washed with $H_2O$ (3×150 mL), dried over anhydrous $Na_2SO_4$, filtered and evaporated. Purification by silica gel chromatography gave the fully protected compound which was dissolved in THF (5 mL) and TBAF (2.5 mmol, 2.5 mL of a 1 M solution in THF) was added and the reaction mixture stirred at room temperature for 2 hours when the reaction was complete. Solvent was carefully removed and the residue purified on a silica gel column to give compound 58 in 66% overall yield.

B) Cytidine BNA Phosphoramidite, (1R,5R,7R,8S)-8-[2-cyanoethoxy(diisopropyl-amino)phosphin oxy]-5-(4,4'-dimethoxytrityloxymethyl)-7-(4-N-benzoyl-cytosin-1-yl)-3-methyl-2,6-dioxa-3-aza-bicyclo[3.2.1]octane (59)

To a solution of Compound 58 (1 mmol) in anhydrous DMF (3.3 mL) was added N,N,N',N'-tetraisopropylamino-2-cyanoethylphosphoramidite (1.75 mmol) and 1-H tetrazole (0.75 mmol). After stirring at room temperature for 15 minutes N-methylimidazole (0.25 mmol) was added. The mixture was stirred an additional 6 hours, then $Et_3N$ (8 mmol) was added. The mixture was poured into EtOAc (100 mL), washed with saturated aqueous $NaHCO_3$ (2×100 mL), dried over anhydrous $Na_2SO_4$, filtered, and evaporated. Purification by silica gel chromatography gave compound 59 in 80% yield.

Example 9

General Procedures for the Preparation of Uridine BNA Phosphoramidite, (1R,5R,7R,8S)-8-[2-cyanoethoxy(diisopropylamino)phosphin oxy]-5-(4,4'-dimethoxytrityloxymethyl)-7-(uridin-1-yl)-3-(2-phenoxy-acetyl)-2,6-dioxa-3-aza-bicyclo[3.2.1]octane (Compound 64)

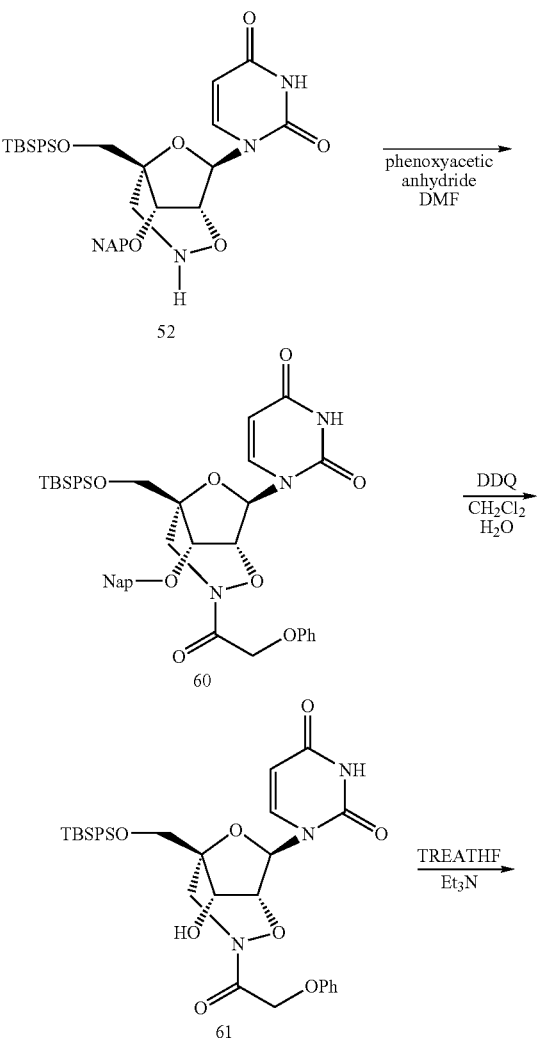

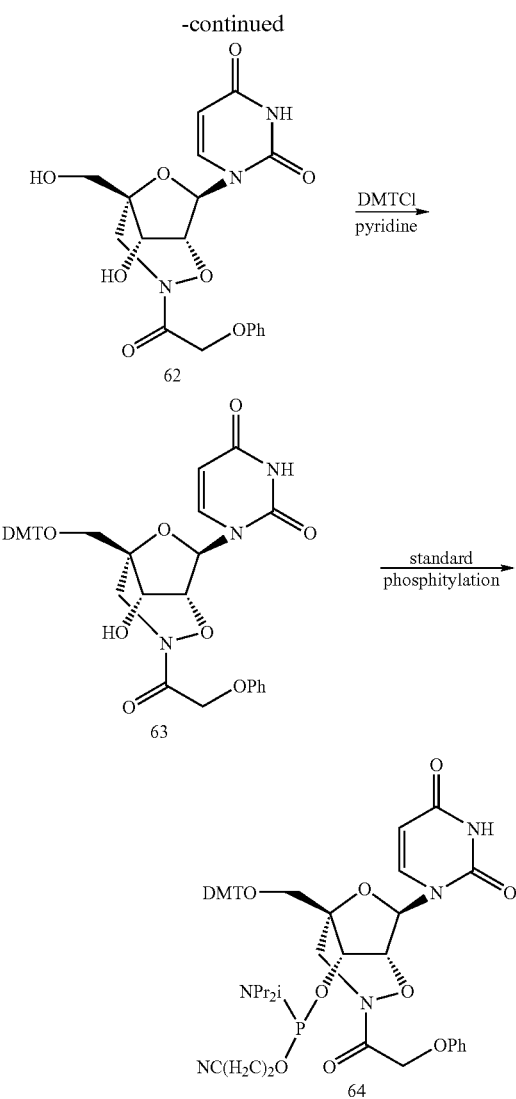

A) 5'-O-tertbutyldiphenylsilyl-3'-O-napthylmethyloxyamino BNA Uridine (60)

To a solution of Compound 52 (4.50 g, 6.92 mmol) in N,N-dimethylformamide (20 mL) was added phenoxyacetic anhydride (2.18 g, 7.62 mmol). After stirring at room temperature for 30 minutes, mixture was poured into EtOAc (500 mL) and washed with aqueous NaHCO₃ (3×400 mL) and H₂O (1×400 mL). Dried over anhydrous Na₂SO₄, filtered, and evaporated to a pale foam. Silica gel purification (1% methanol in CH₂Cl₂) yielded 4.67 g (86%) of compound 60 as a pale yellow foam.

B) 5'-O-tertbutyldiphenylsilyl-N-phenoxyacetyl-oxyamino BNA Uridine (61)

2,3-Dichloro-5,6-dicyano-1,4-benzoquinone (11.0 g, 48.4 mmol) was added to a solution of compound 60 (4.76 g, 6.08 mmol) in CH₂Cl₂ (65 mL) and H₂O (13 mL). After 12 hours of vigorous stirring at room temperature, the mixture was poured into CH₂Cl₂ (500 mL). The resulting solution was washed with 2% (w/v) aqueous sodium bisulfite, followed by saturated aqueous NaHCO₃, then dried over anhydrous Na₂SO₄, filtered, and evaporated to a red foam. Purification by silica gel chromatography (2.5% methanol in CH₂Cl₂) yielded 3.30 g (84%) of Compound 61 as a beige foam.

C) N-phenoxyacetyl-oxyamino BNA Uridine (62)

To a solution of compound 61 (1.29 g, 2.01 mmol) in anhydrous CH₂Cl₂ (6 mL) was added triethylamine (559 μL, 4.01 mmol) and triethylamine trihydrogenfluoride (653 μL, 4.01 mmol). After stirring at room temperature for 16 hours the mixture was loaded directly onto a silica gel column. Elution with 8% methanol in CH₂Cl₂ and subsequent evaporation yielded 742 mg (91%) of Compound 62 as an off-white solid.

D) 1-[5-[Bis-(4-methoxy-phenyl)-phenyl-methoxymethyl]-8-hydroxy-3-(2-phenoxy-acetyl)-2,6-dioxa-3-aza-bicyclo[3.2.1]oct-7-yl]-1H-pyrimidine-2,4-dione (63)

To a solution of compound 62 (736 mg, 1.82 mmol) in anhydrous pyridine (7 mL) was added 4-N,N-dimethylaminopyridine (33 mg, 0.27 mmol) and 4,4'-dimethoxytrityl chloride (923 mg, 2.72 mmol). After stirring at room temperature for 6 hours the reaction mixture was quenched with methanol and concentrated in vacuo. The residue was dissolved in CH₂Cl₂ (250 mL), washed with saturated aqueous NaHCO₃, dried over Na₂SO₄, filtered, and evaporated. Purification by silica gel chromatography (2.5% methanol in CH₂Cl₂) yielded 1.28 g (99%) of compound 63 as a pale foam.

E) Uridine BNA Phosphoramidite, (1R,5R,7R,8S)-8-[2-cyanoethoxy(diisopropylamino)-phosphinoxy]-5-(4,4'-dimethoxytrityloxymethyl)-7-(uridin-1-yl)-3-(2-phenoxy-acetyl)-2,6-dioxa-3-aza-bicyclo[3.2.1]octane (Compound 64)

To a solution of compound 63 (1.25 g, 1.77 mmol) in anhydrous DMF (4.4 mL) was added N,N,N',N'-tetraisopropylamino-2-cyanoethylphosphoramidite (898 μL, 2.83 mmol) and tetrazole (62 mg, 0.88 mmol). The mixture was stirred at room temperature for 15 minutes, followed by the addition of N-methylimidazole (35 μL, 0.44 mmol). The mixture was stirred for an additional 5 hours, at which time triethylamine (350 μL, 2.47 mmol) was added. The mixture was poured into EtOAc (300 mL), washed with saturated aqueous NaHCO₃ (2×100 mL), dried over anhydrous Na₂SO₄, filtered, and evaporated. Purification by silica gel chromatography (1:1 hexanes:EtOAc) gave 1.34 g (83%) of compound 64 as a white foam.

Example 10

General Procedures for the Preparation of Cytidine BNA Phosphoramidite, (1R,5R,7R,8S)-8-[2-cyanoethoxy(diisopropylamino)phosphin oxy]-5-(4,4'-dimethoxytrityloxymethyl)-7-(4-N-benzoyl-cytosin-1-yl)-3-(2-phenoxy-acetyl)-2,6-dioxa-3-aza-bicyclo[3.2.1]octane (69)

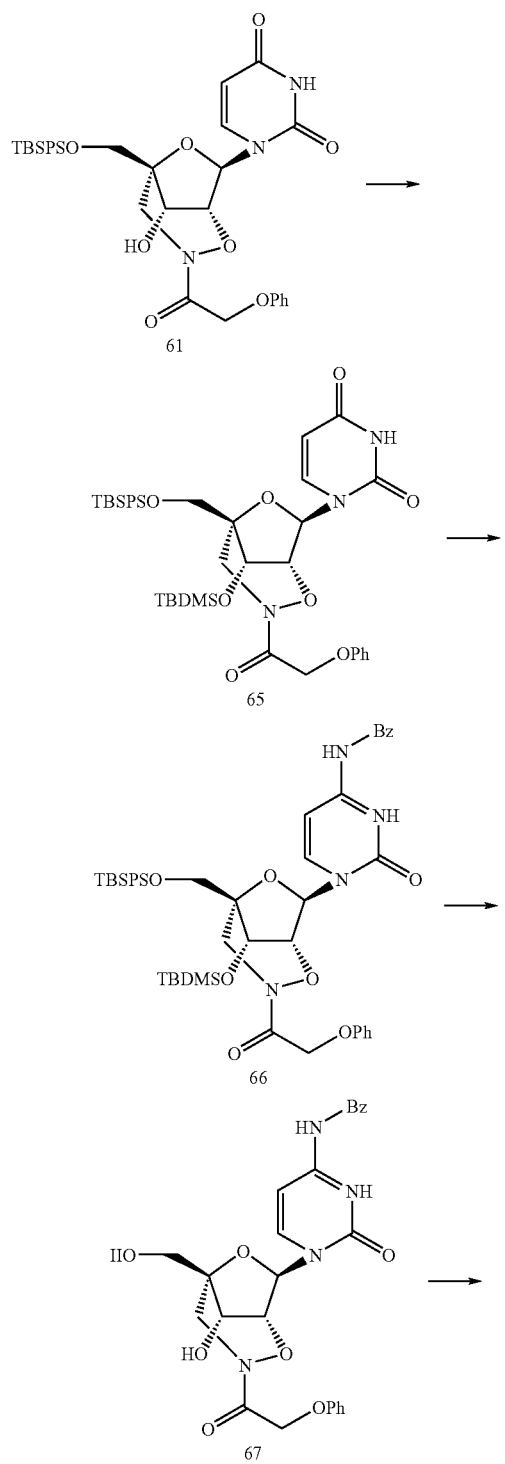

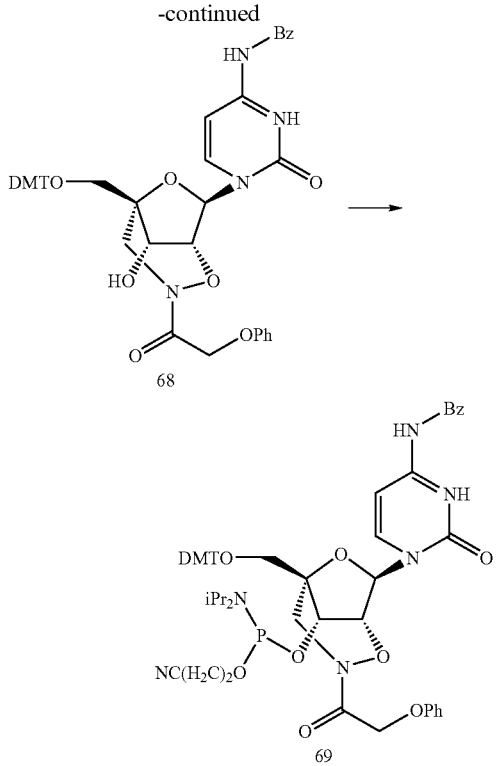

A) 5'-O-tertbutyldiphenylsilyl-3'-O-tertbutyldimethylsilyl-N-phenoxyacetyl-oxyamino BNA Uridine (65)

To a solution of compound 61 (4.87 g, 7.57 mmol) in DMF (20 mL) was added imidazole (14.4 g, 212 mmol) and tert-butyldimethylsilyl chloride (13.7 g, 90.8 mmol). After stirring at room temperature for 26 hours, the mixture was poured into EtOAc (400 mL), washed with saturated aqueous NaHCO$_3$, washed with brine, dried over Na$_2$SO$_4$, filtered, and evaporated to a pale oil. Purification by silica gel chromatography (3:2 hexanes:EtOAc) yielded 4.98 g (86%) of Compound 65 as a white foam.

B) 5'-O-tertbutyldiphenylsilyl-3'-O-tertbutyldimethylsilyl-N-phenoxyacetyl-oxyamino BNA N$^4$-benzoyl Cytidine (66)

To a chilled (0° C.) suspension of 1,2,4-triazole (6.28 g, 90.9 mmol) in CH$_3$CN (70 mL) was added phosphorus oxychloride (2.42 mL, 25.97 mmol) dropwise with stirring. After stirring this mixture at 0° C. for 20 minutes, triethylamine (18.1 mL, 130 mmol) was added. To this chilled mixture was added a solution of compound 65 (4.92 g, 6.49 mmol) in CH$_2$Cl$_2$ (16 mL). The mixture was warmed to room temperature and stirred for 5 hours. The resulting solution was poured into CH$_2$Cl$_2$ (600 mL), washed with saturated NaHCO$_3$ and brine, dried over anhydrous Na$_2$SO$_4$, filtered, then evaporated to a yellow foam. This residue was redissolved in anhydrous 1,4-dioxane (50 mL), then added to a solution of benzamide (4.72 g, 39 mmol) and sodium hydride (32 mmol) in 1,4-dioxane (50 mL). After 30 minutes at room temperature, the mixture was poured into CH$_2$Cl$_2$, washed with NaHCO$_3$, dried over anhydrous Na$_2$SO$_4$, filtered, and evaporated to a yellow solid. Purification by silica gel chromatography (0.5% methanol in CH$_2$Cl$_2$) yielded 3.93 g (70%) of Compound 66 as a pale yellow solid.

C) N-{1-[8-Hydroxy-5-hydroxymethyl-3-(2-phe-noxy-acetyl)-2,6-dioxa-3-aza-bicyclo [3.2.1]oct-7-yl]-2-oxo-1,2-dihydro-pyrimidin-4-yl}-benzamide (67)

To a solution of Compound 66 (3.92 g, 4.55 mmol) in anhydrous CH$_2$Cl$_2$ (150 mL) was added triethylamine (6.34 mL, 45.5 mmol) and triethylamine trihydrogenfluoride (7.41 mL, 45.5 mmol). After stirring at room temperature for 4 days the mixture was loaded directly onto a silica gel column. Elution with 5% methanol in CH$_2$Cl$_2$ and subsequent evaporation yielded 1.81 g (78%) of compound 67 as an off-white solid.

D) N-{1-[5-[Bis-(4-methoxy-phenyl)-phenyl-methoxymethyl]-8-hydroxy-3-(2-phenoxy-acetyl)-2,6-dioxa-3-aza-bicyclo[3.2.1]oct-7-yl]-2-oxo-1,2-dihydro-pyrimidin-4-yl}-benzamide (68)

To a solution of Compound 67 (1.80 g, 3.54 mmol) in anhydrous pyridine (15 mL) was added 4-N,N-dimethylaminopyridine (65 mg, 0.53 mmol) and 4,4'-dimethoxytrityl chloride (2.04 g, 6.02 mmol). After stirring at room temperature for 6 hours the reaction mixture was quenched with methanol and concentrated in vacuo. The residue was dissolved in CH$_2$Cl$_2$ (300 mL), washed with saturated aqueous NaHCO$_3$, dried over Na$_2$SO$_4$, filtered, and evaporated. Purification by silica gel chromatography (2% methanol in CH$_2$Cl$_2$) yielded 2.37 g (82%) of Compound 68 as a pale yellow foam.

E) Cytidine BNA Phosphoramidite, (1R,5R,7R,8S)-8-[2-cyanoethoxy(diisopropyl-amino)phosphin oxy]-5-(4,4'-dimethoxytrityloxymethyl)-7-(4-N-benzoyl-cytosin-1-yl)-3-(2-phenoxy-acetyl)-2,6-dioxa-3-aza-bicyclo[3.2.1]octane (69)

To a solution of Compound 68 (2.22 g, 2.74 mmol) in anhydrous DMF (6.9 mL) was added N,N,N',N'-tetraisopropylamino-2-cyanoethylphosphoramidite (1.3 mL, 4.11 mmol) and tetrazole (96 mg, 1.37 mmol). The mixture was stirred at room temperature for 15 minutes, followed by the addition of N-methylimidazole (55 µL, 0.68 mmol). The mixture was stirred for an additional 4.5 hours, at which time triethylamine (534 µL, 3.83 mmol) was added. The mixture was poured into EtOAc (250 mL), washed with saturated aqueous NaHCO$_3$ (2×100 mL), dried over anhydrous Na$_2$SO$_4$, filtered, and evaporated. Purification by silica gel chromatography (57% hexanes/43% EtOAc) gave 2.78 g (85%) of Compound 69 as an off-white foam.

Example 11

General Procedures for the Preparation of Nucleoside 6'-(R)-methyl BNA Phosphoramidite, (1S,3R,4R,6R,7S)-7-[2-cyanoethoxy(diisopropylamino)phosphin oxy]-1-(4,4'-dimethoxytrityloxymethyl)-3-(pyrimidine-1-yl or purine-9-yl)-6-methyl-2,5-dioxabicyclo[2.2.1]heptane (Compound 77)

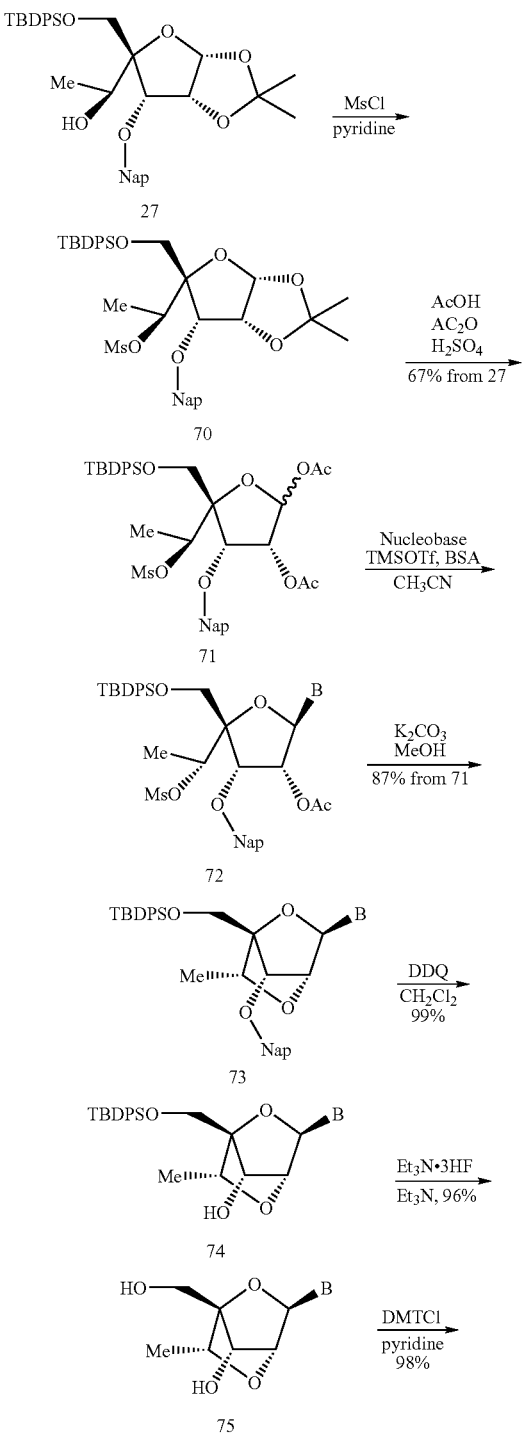

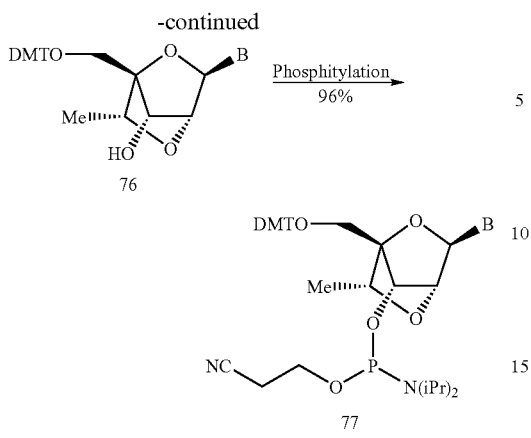
This general procedure is amenable to specific modifications as illustrated in previous examples shown herein. Compound 27 is obtained as illustrated in Example 5.
Example 12
General Procedures for the Preparation of (1S,3R, 4R,7S)-7-[2-cyanoethoxy(diisopropyl-amino)phosphinoxy]-1-[1-(S)-(4,4'-dimethoxytrityl)oxy-ethyl]-3-(uracil-1-yl)-2,5-dioxa-bicyclo[2.2.1]heptane (Compound 95)
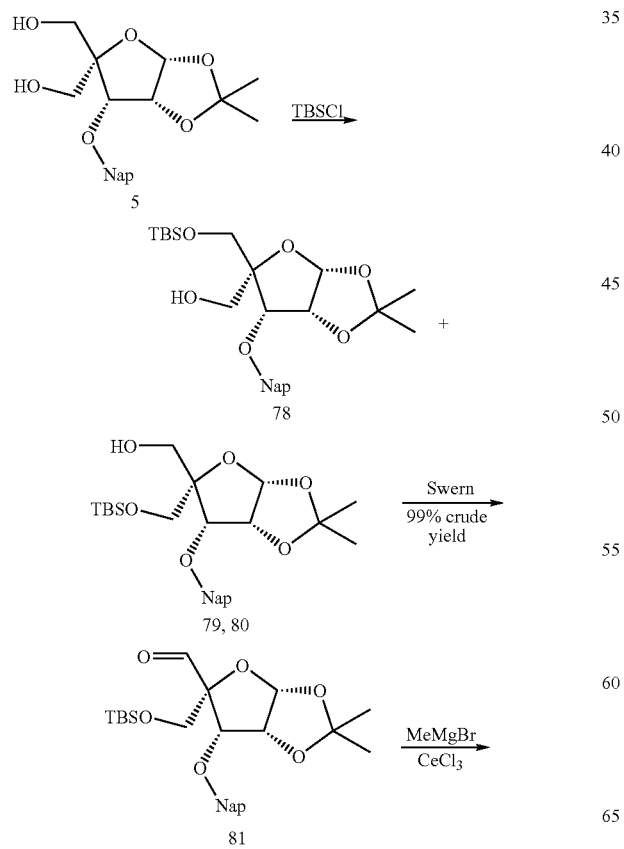
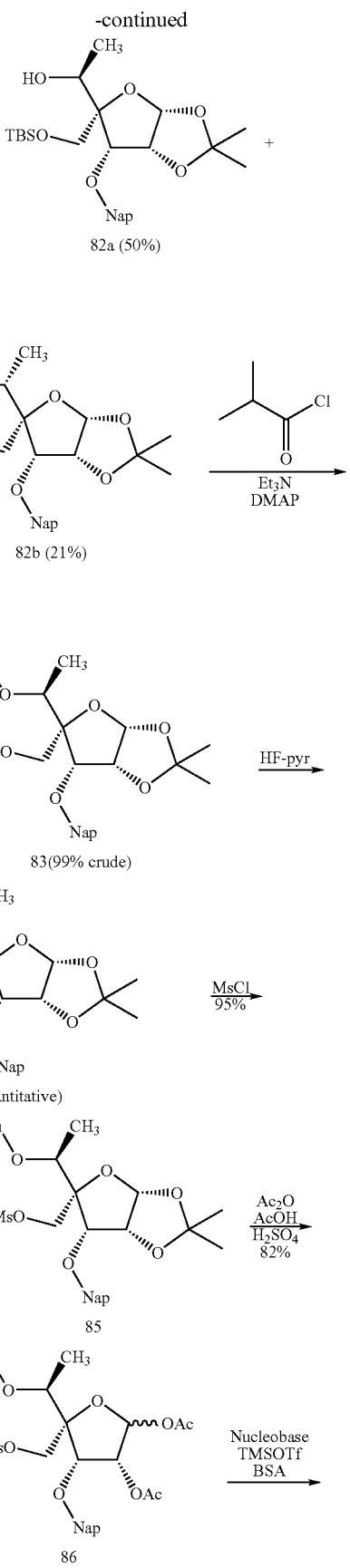

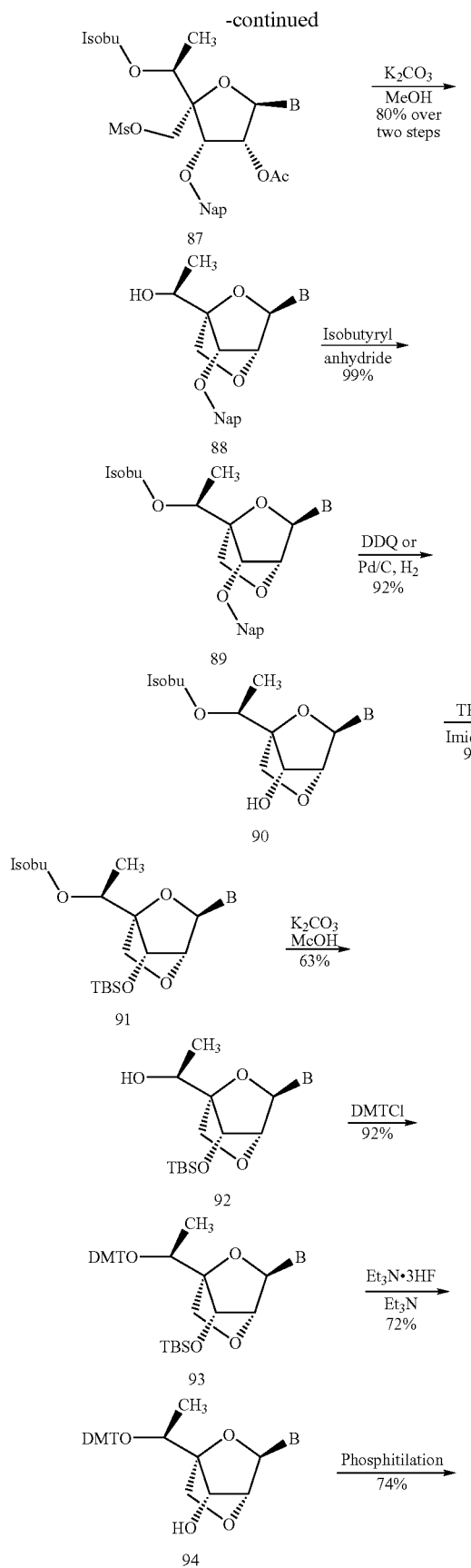

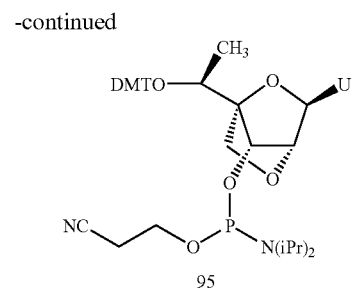

The 5'-(S)-isomer Compound 95 is shown but the 5'-(R)-isomer can also be prepared using Compound 82b instead of 82a.

Example 13

General Procedure for the Preparation of uridine-alpha-L-phosphoramidite (1S,3R,4S,7S)-7-(2-Cyanoethoxy(diisopropylamino)-phosphinoxy)-1-(4,4'-dimethoxytrityloxymethyl)-3-(uridin-1-yl)-2,5-dioxabicyclo[2.2.1]heptane (113)

A) Preparation of 3'-O-Naphthyl-4-(hydroxymethyl)-1,2-O-isopropylidene-α-D-threo-pentofuranose (100)

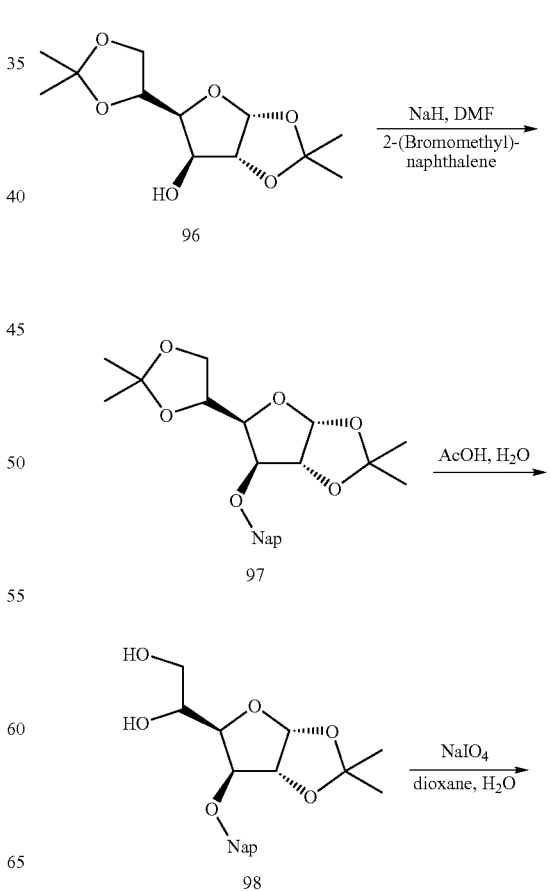

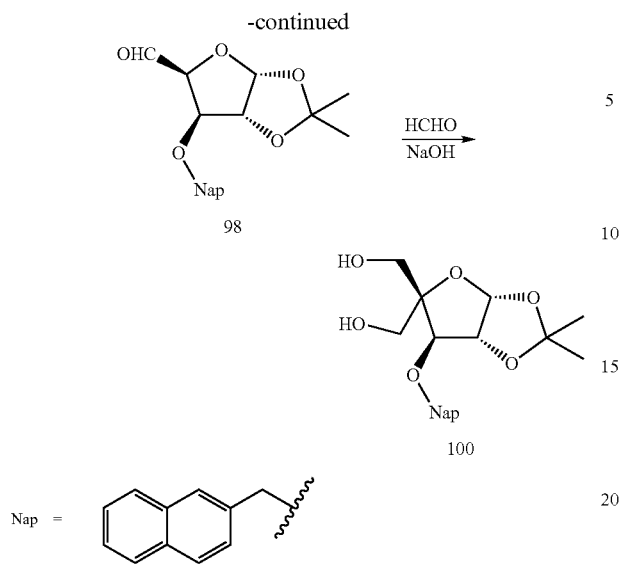

A similar experimental procedure described earlier for the preparation of compound 5 was used to make compound 100 from commercially available 1,2:5,6-Di-O-alpha-D-glucofuranose (96). The yields at each step were comparable to the preparation described earlier in the application.

B) Preparation of 3-O-naphthyl-5-O-(methanesulfonyl)-4-C-[[(methanesulfonyl)oxy]-methyl]-1,2-O-isopropylidene-b-L-threo-pentofuranose (101)

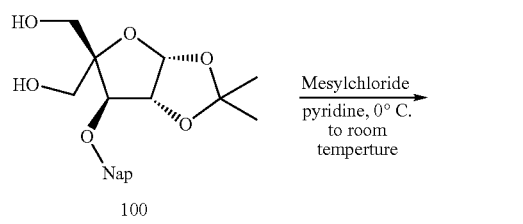

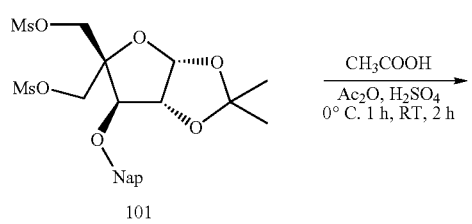

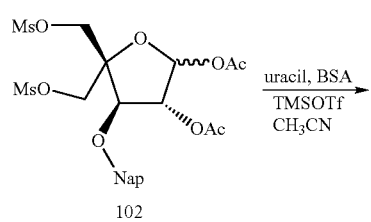

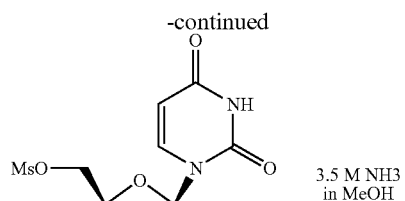

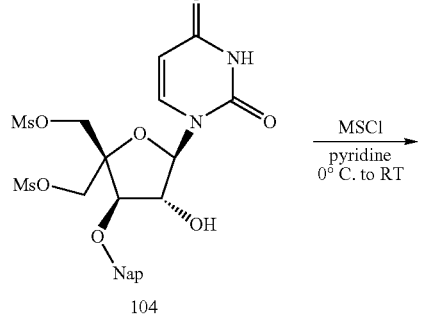

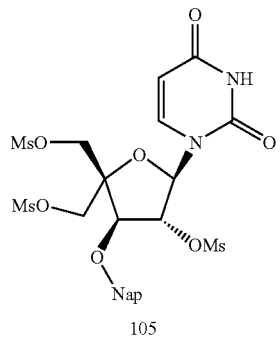

Compound 100 (23 g 63.8 mmol) was dissolved in anhydrous pyridine (125 mL) and the solution was cooled to 0° C. in an ice/salt bath. After 5 minutes at this temperature, methanesulfonylchloride (18 mL) was slowly added to the reaction mixture followed by stirring at 0° C. for 2 h. The bath was removed and the reaction mixture was stirred at room temperature for additional 3 h. The mixture was diluted with ethylacetate (200 mL) and washed with aqueous saturated sodium bicarbonate solution (3×100 mL), water (2×100 mL) and finally brine (100 mL). The organic layer was separated and dried over anhydrous sodium sulfate. Solvent was removed and the residue azeotroped with toluene to remove most of the pyridine. The resulting oil was purified on silica gel using 3-7% MeOH in dichloromethane. Appropriate fractions collected concentrated to oil which was dried under reduced pressure to give Compound 101 in 88% yield.

C) Preparation of 1,2-Di-O-acetyl-3-O-naphthyl-5-O-(methanesulfonyl)-4-C-[[(methanesulfonyl)oxy]-methyl]-L-threo-pentofuranose (102)

Compound 101 (26.0 g) was dissolved in a mixture of glacial acetic acid (100 mL) and acetic anhydride (25 mL) and the reaction mixture was cooled to 0° C. in ice/salt bath. After cooling the reaction mixture for 5-7 minutes, concentrated sulfuric acid (3 drops) was added over 5 minute period. The reaction mixture was then stirred at this temperature for 1 h and then at room temperature for additional 2 h. The mixture was diluted with $CH_2Cl_2$ (500 mL) and carefully washed with water (5×100 mL) followed by brine (3×100 mL). The organic layer was concentrated to an oil and dried for 24 h at reduced pressure to give Compound 102 as a an oil (yield=28.3 g).

D) Preparation of 1-(2-O-acetyl-3-O-naphthylmethyl-5-O-(methanesulfonyl-4-C-[[(methanesulfonyl)oxy]-methyl]-α-L-threo-pentofuranosyl]-uracil (103)

Uracil (8.4 g) and Compound 102 (28 g) from the previous step were combined together in a round bottomed flask and anhydrous $CH_3CN$ (250 mL) was added. To this stirred suspension was added BSA (58.5 mL) and the reaction mixture was heated at bath temperature of 85° C. for 2 h. The heating bath was removed and the flask was allowed to cool for 10 minutes and then placed in an ice bath and cooled for about 10 minutes. TMSOTf (20 mL) was added very slowly over 15 minutes under an atmosphere of argon. After the addition was complete the ice bath was removed and the reaction vessel was allowed to warm before placing it in preheated bath (69° C.) for 5 h. The reaction mixture was cooled in an ice bath and saturated bicarbonate solution was added carefully. The mixture was diluted with ethylactetate (400 mL), carefully washed with saturated bicarbonate solution (5×200 mL) and then washed with brine. All organic washings were combined and concentrated to an oil which was purified by 20 to 40% ethyl acetate in hexanes. Appropriate fractions were combined, concentrated to off white foam and dried under high vacuum for 15 h (yield was 24.82 g, ~82%).

E) Preparation of 1-(3-O-naphthylmethyl-5-O-(methanesulfonyl-4-C-[[(methane-sulfonyl)oxy]-methyl]-α-L-threo-pentofuranosyl]-uracil (104)

Crude compound 103 (23 g) was dissolved in 200 mL of 3.5 M $NH_3$ solution in MeOH and the reaction mixture was stirred. After 2 h. TLC (20% acetone/$CH_2Cl_2$) indicated that the reaction was complete. The solvent was removed and traces of ammonia removed by azeotroping with MeOH. Finally, the residue was dried under high vacuum to furnish a foam. The foam was purified on silica gel using 20% acetone in dichloromethane followed by eluting the compound with 10% MeOH in acetone. Appropriate fractions were collected and concentrated to furnish a colorless solid. The solid was dried under high vacuum for 12 h to give Compound 104 in a 64% yield.

F) Preparation of 1-(2-O-methanesulfonyl-3-O-naphthylmethyl-5-O-(methanesulfonyl-4-C-[[(methane-sulfonyl)oxy]-methyl]-α-L-threo-pentofuranosyl]-uracil (105)

To a cold solution of compound 104 (12.5 g) in anhydrous pyridine (50 mL) was added methanesulfonylchloride (2.1 mL) followed by stirring at 0° C. for 30 minutes and then an additional 4 h at room temperature. The reaction was monitored by LCMS. The reaction mixture was diluted with ethylacetate (200 mL) and washed with saturated sodium bicarbonate solution (3×150 mL) followed by brine (100 mL). The organic layer was dried over anhydrous sodium sulfate and concentrated to a foam which after silica gel purification using 7% MeOH in dichloromethane gave compound 105 in 90% isolated yield.

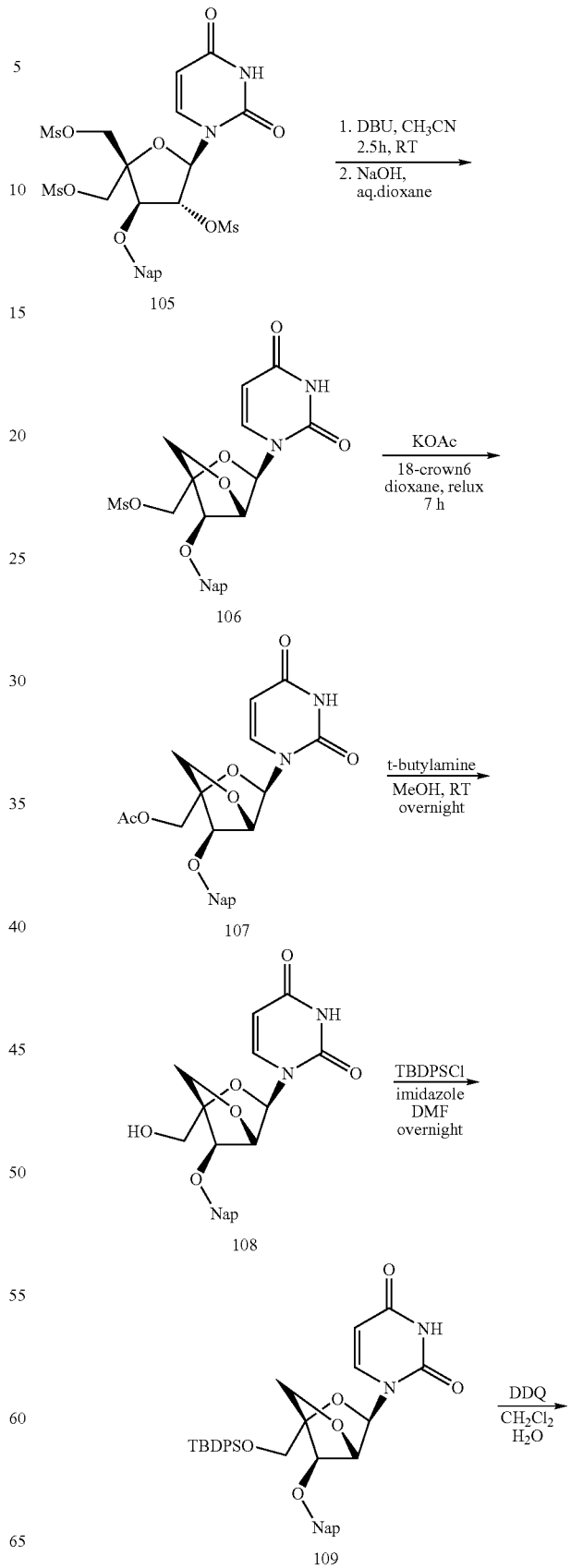

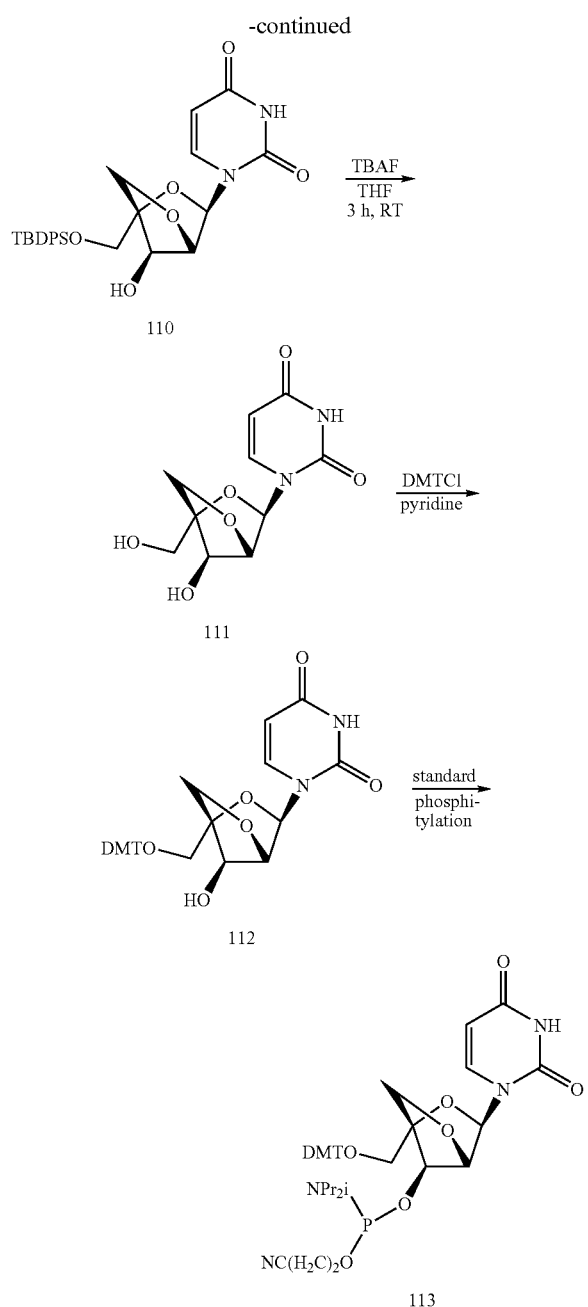

G) Preparation of (1S,3R,4S,7R)-1-(methanesulfon-oxymethyl)-7-napthylmethyloxy-3-(uracil-1-yl)-2,5-dioxabicyclo[2.2.1]heptane (106)

Compound 105 (14.0 g) was dissolved in acetonitrile (180 mL) and DBU (8 mL) was added. The reaction mixture was stirred at room temperature for 2.5 hours. A white cake precipitated out which was separated by filtration and the solid washed with acetonitrile followed by diethylether. The solid was dried at room temperature under high vacuum for 15 h. The mother liquor was concentrated to yellow residue, taken up in ethylactetate (100 mL) and washed with 2N aqueous HCl followed by saturated bicarbonate solution and water. The ethylacetate layer was concentrated to dryness. The desired anhydro compound was taken up in 1,4-dioxane (130 mL) and to this was added 2N NaOH (30 mL). The reaction mixture was stirred at room temperature for 5 hours and the mixture was neutralized with acetic acid. The solvent was removed under reduced pressure and the residue purified by silica gel column. Thy solvent removed under reduced pressure and the residue dried under vacuum to furnish Compound 106 in 94% isolated yield.

H) Preparation of (1S,3R,4S,7R)-1-(Acetoxymethyl)-7-napthylmethyloxy-3-(uracil-1-yl)-2,5-dioxabicyclo[2.2.1]heptane (107)

Compound 106 (9.6 g) was suspended in 1,4-dioxane (500 mL). To this suspension added potassium acetate (10.03 g) and 18-crown-6 (1.11 g). The reaction mixture was heated at gentle reflux with stirring for 5 h. TLC (10% MeOH in $CH_2Cl_2$) on silica-gel indicated that the reaction was complete. The reaction mixture was brought to room temperature and solvent removed under reduced pressure. The residue was taken up in $CH_2Cl_2$ (200 mL) and washed with water (3×100 mL). The organic layer was concentrated to dryness and dried under high vacuum for two hours to provide crude Compound 107 as a colorless foam. The foam was used without further purification for the next step. Crude weight was 10.0 g.

I) Preparation of (1S,3R,4S,7R)-1-(hydroxymethyl)-7-napthylmethyloxy-3-(uracil-1-yl)-2,5-dioxabicyclo[2.2.1]heptane (108)

Tertiary butylamine (8.5 g, 12 mL) was added to crude Compound 107 dissolved in anhydrous MeOH (100 mL) to give a final concentration of ~1M butylamine in MeOH. The reaction mixture was stirred at room temperature for 15 hours when the deacylated compound precipitated out. The TLC (10% MeOH in $CH_2Cl_2$) indicated the reaction was complete. The solvent was removed under reduced pressure to give a colorless solid. Yield after drying was 99%.

J) Preparation of (1S,3R,4S,7R)-1-(t-butyldiphenyl-silyloxymethyl)-7-napthylmethyloxy-3-(uracil-1-yl)-2,5-dioxabicyclo[2.2.1]heptane (109)

Imidazole (5.5 g) was added to Compound 108 (8.83 g) dissolved in anhydrous DMF (100 mL) followed by addition of t-butyldiphenylsilylchloride (8.5 mL). The reaction mixture was stirred for 15 h at room temperature when it was complete. The reaction mixture was diluted with EtOAc (400 mL) and washed with saturated sodium bicarbonate solution (3×500 mL) followed by water (2×200 mL). The organic layer was dried over anhydrous sodium sulfate and the solvent was removed under reduced pressure. Finally the residue was purified on a silica gel column using 30% EtOAc in $CH_2Cl_2$ as the eluant. Appropriate fractions were collected and concentrated to give Compound 109 in 78% yield.

K) Preparation of (1S,3R,4S,7R)-1-(t-butyldiphenyl-silyloxymethyl)-7-hydroxy-3-(uracil-1-yl)-2,5-dioxabicyclo[2.2.1]heptane (110)

Water (23 mL) was added to Compound 109 (11.8 g) dissolved in $CH_2Cl_2$ (120 mL) and the biphasic solution was stirred at room temperature. To this stirring solution was added DDQ (9.2 g) and the reaction mixture was stirred for 7 h at which point the reaction was complete. The reaction mixture was diluted with dichloromethane (500 mL) and it washed with 2% aqueous sodium bisulfite solution. The organic layer was separated and the aqueous layer was extracted several times with dichloromethane. The combined organic layer was washed with saturated sodium bicarbonate solution (5×300 mL). The organic layer was dried over anhydrous sodium sulfate and the solvent removed under reduced pressure. The residue was purified by using 30% EtOAc in CH$_2$Cl$_2$ followed by 10% MeOH in CH$_2$Cl$_2$. Compound 110 obtained in a 96% yield as colorless pallets after removing the solvent.

L) Preparation of (1S,3R,4S,7R)-7-hydroxy-1-(hydroxymethyl)-3-(uracil-1-yl)-2,5-dioxabicyclo[2.2.1]heptane (111)

Compound 110 (8.7 g) was dissolved in anhydrous THF (80 mL) and TBAF (5.05 g, 20 mL of 1 M solution in THF) was added and the reaction mixture stirred at room temperature for 3 hours at which time the reaction was complete. The solvent was carefully removed and the residue purified on silica gel column to give Compound 111 in 90% yield.

M) Preparation of (1S,3R,4S,7R)-1-(4,4'-dimethoxytrityloxymethyl)-7-hydroxy-3-(uracil-1-yl)-2,5-dioxabicyclo[2.2.1]heptane (112)

A mixture of compound III (3.31 g, 12.9 mmol) and dimethoxytrityl chloride (5.7 g, 16.8 mmol) was dried together in a round bottomed flask on P$_2$O$_5$ and under high vacuum pressure for ~12 h. To this mixture, anhydrous pyridine (100 mL) was added and the resulting solution stirred for 8 h. TLC (5% MeOH/CH$_2$Cl$_2$) indicated the reaction was complete. The mixture was diluted with ethylacetate (200 mL), washed with water (2×300 mL) and saturated aqueous sodium bicarbonate solution (2×100 mL). The aqueous layer was back extracted with ethylacetate (2×50 mL) and the combined organic layers were washed with water (100 mL). The organic layer was dried over anhydrous sodium sulfate. The solvent was removed under reduced pressure to furnish a light yellow foam, which was purified on silica gel column using 5% MeOH in CH$_2$Cl$_2$ as the eluant. Appropriate fractions were collected and concentrated to a solid which was azeotroped with anhydrous acetonitrile (3×50 mL). The resultant solid was dried under high vacuum for 20 h to give compound 112 in 96% yield.

M) Preparation of (1S,3R,4S,7R)-7-(2-cyanoethoxy(diisopropylamino)phosphinoxy)-1-(4,4'-dimethoxytrityloxymethyl)-3-(uracil-1-yl)-2,5-dioxabicyclo[2.2.1]heptane (113)

Dried 1-H tetrazole (0.45 g) and N-methylimidazole (0.176 g) were added to Compound 112 (4.0 g) dissolved in anhydrous DMF (35 mL). The reaction mixture was stirred for few minutes and N,N,N',N'-tetraisopropylamino-2-cyanoethylphosphoramidite (3.26 g) was added with stirring for 8 hours. The reaction was complete and it was taken up in EtOAc (100 mL) washed with saturated aqueous NaHCO$_3$ (2×100 mL), dried over anhydrous Na$_2$SO$_4$, filtered, and evaporated. Purification by silica gel chromatography (15% acetone in dichloromethane) gave Compound 113 as colorless foam in 98% yield (5.13 g).

Example 14

General Procedure for the Preparation of N-4-benzoyl-cytidine-alpha-L-phosphoramidite (1S,3R,4S,7S)-7-[2-cyanoethoxy(diisopropylamino)-phosphinoxy]-1-[[(4,4'-dimethoxy-trityl)oxy]methyl]-3-(4-N-benzoyl-cytosin-1-yl)-2,5-dioxabicyclo[2.2.1]heptane (119)

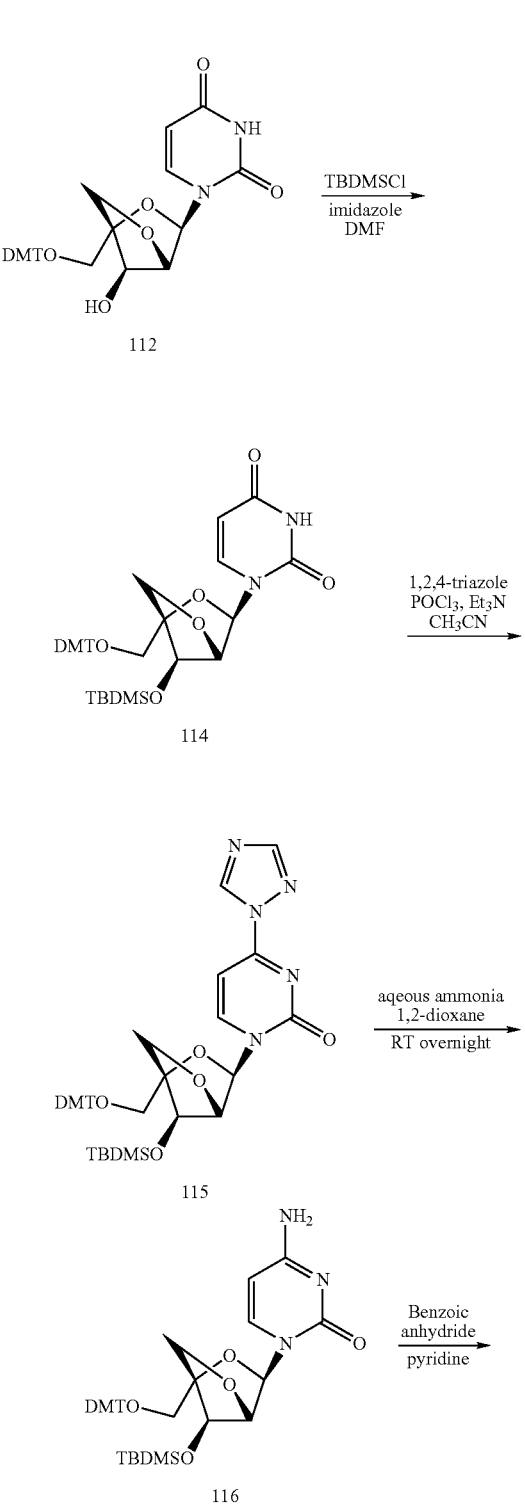

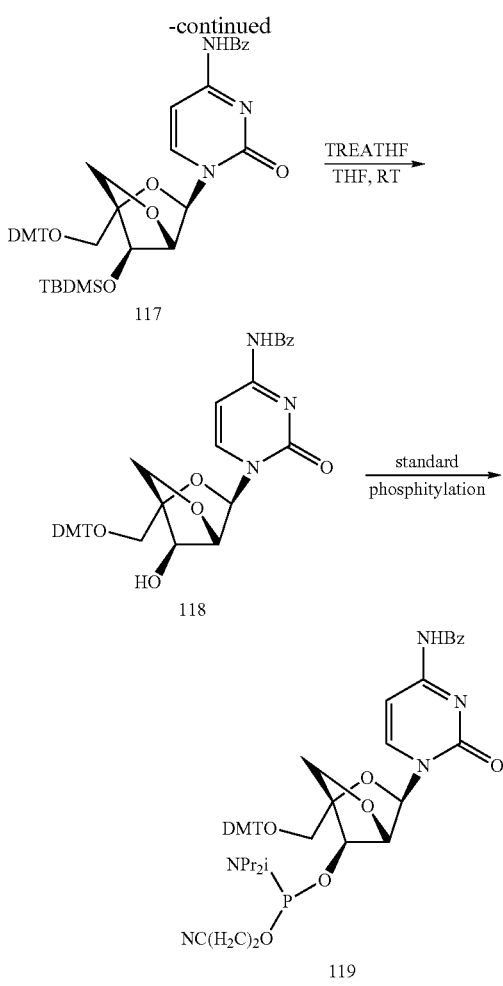

A) Preparation of (1S,3R,4S,7R)-7-(t-butyldimethyl-silyloxy)-1-(4,4'-dimethoxy-trityloxymethyl)-3-(uracil-1-yl)-2,5-dioxabicyclo[2.2.1]heptane (114)

A solution of compound 112 (1.5 g) in anhydrous DMF (10 mL) was stirred with imidazole (0.913 g), trethylamine (375 μL) and t-butyldimethylsilylchloride (0.81 g) for 15 h. The reaction mixture was diluted with EtOAc (40 mL) and washed with aqueous sodium bicarbonate solution (2×20 mL). The organic layer was separated and dried over anhydrous $Na_2SO_4$. The solvent was removed and the product purified on silica gel using 10% acetone in $CH_2Cl_2$. The appropriate fractions were concentrated and dried to give Compound 114 in 94% yield.

B) Preparation of (1S,3R,4S,7R)-7-(t-butyldimethyl-silyloxy)-1-(4,4'-dimethoxy-trityloxymethyl)-3-(cytosin-1-yl)-2,5-dioxabicyclo[2.2.1]heptane (116)

1,2,4-triazole (2.16 g) was suspended in anhydrous acetonitrile (10 mL) and cooled in an ice bath for 10 minutes. To this cold solution $POCl_3$ (1.3 g) was added and the reaction mixture was stirred at cold temperature for 10 minutes. Triethylamine (6.2 mL) was added slowly over 20 minutes keeping the reaction vessel cold. After the addition was complete, the reaction mixture was stirred for additional 30 to 35 minutes. A solution of compound 114 (1.5 g) in anhydrous acetonitrile (5 mL) was cannulated into the triazolide and the flask was washed with additional $CH_3CN$ (2 mL) which was added to the flask containing the reaction mixture. The reaction mixture was stirred at room temperature for an additional 1.5 h at which time the reaction was complete. Triethylamine (5 mL) was added to the reaction mixture followed by EtOAc (50 mL). The mixture was washed with aqueous sodium bicarbonate solution (2×20 mL) and brine (2×20 mL). The organic layer was dried over anhydrous sodium sulfate and the solvent removed under reduced pressure and the resulting foam dried under vacuum to yield compound 115 as a off white foam. Crude Compound 115 was used for the next step without further purification.

Crude 115 was stirred with 1:1 30% $NH_4OH$ in 1,4-dioxane (30 mL) for 3 h. The reaction mixture was concentrated to dryness and purified on silica gel using 10-15% MeOH in $CH_2Cl_2$ to yield compound 116 in 90% yield.

C) Preparation of (1S,3R,4S,7R)-3-(4-N-benzoyl-cytosin-1-yl)-7-1-[[(4,4'-dimethoxytrityl)oxy]methyl]-7-(t-butyldimethylsilyoxy)-2,5-dioxabicyclo2.2.1]heptane (117)

A solution of compound 116 (1.0 g) and benzoic anhydride (0.675 g) in anhydrous pyridine (7 mL) was stirred at room temperature for 18 h. The solution was diluted with EtOAc (30 mL) and washed with saturated sodium bicarbonate solution (3×50 mL). The organic layer was separated and dried on anhydrous $Na_2SO_4$. The solvent was removed under reduced pressure and the residue purified on silca gel column using 5% MeOH in $CH_2Cl_2$ as the eluant. Appropriate fractions were collected and concentrated to give compound 117 as colorless foam in 96% isolated yield.

D) Preparation of (1S,3R,4S,7R)-3-(4-N-benzoyl-cytosin-1-yl)-7-1-[[(4,4'-dimethoxytrityl)oxy]methyl]-7-hydroxy-2,5-dioxabicyclo[2.2.1]heptane (118)

A solution of compound 117 (1.02 g), triethylaminetrihydrogenfluoride (1.8 mL) and triethylamine (1.5 mL) in anhydrous THF were stirred at room temperature for 2 days. The reaction mixture was diluted with EtOAc (40 mL) and the organic layer was washed with aqueous saturated sodium bicarbonate solution (5×30 mL) followed by water (30 mL). The organic layer was dried over anhydrous sodium sulfate and concentrated to dryness. The resultant residue was purified on silca gel chromatography using 5% MeOH in $CH_2Cl_2$. The appropriate fractions were concentrated to furnish Compound 118 in 98.5% yield.

E) Preparation of (1S,3R,4S,7S)-7-[2-cyanoethoxy (diisopropylamino)-phosphinoxy]-1-[[(4,4'-dimethoxytrityl)oxy]methyl]-3-(4-N-benzoyl-cytosin-1-yl)-2,5-dioxabicyclo[2.2.1]heptane (119)

To a solution of compound 118 (0.7 g) in anhydrous DMF (5 mL) was added 1-H tetrazole (70 mg) followed by the addition of N-methylimidazole (25 μL). To this solution was added N,N,N',N'-tetraisopropylamino-2-cyanoethylphosphoramidite (0.51 mL). The mixture was stirred for an additional 8 h. The mixture was poured into EtOAc (100 mL), washed with saturated aqueous $NaHCO_3$ (2×100 mL), dried over anhydrous $Na_2SO_4$, filtered and evaporated. Purification by silica gel chromatography using 40% acetone in dichloromethane gave compound 119 in 87% isolated yield.

What is claimed is:

1. A compound having formula I:

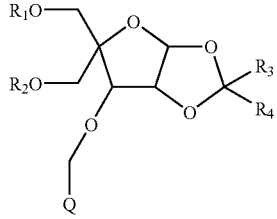

wherein:
- $R_1$ is H or a hydroxyl protecting group;
- $R_2$ is H or a hydroxyl protecting group;
- $R_3$ and $R_4$ are each independently $C_1$-$C_6$ alkyl or substituted $C_1$-$C_6$ alkyl; and
- Q is an optionally substituted polycyclylic aromatic or heteroaromatic radical.

2. The compound of claim 1 wherein said optionally substituted polycyclylic aromatic or heteroaromatic radical comprises from 2 to about 5 fused rings.

3. The compound of claim 2 wherein Q comprises two fused rings.

4. The compound of claim 2 wherein Q comprises at least one heteroaromatic ring.

5. The compound of claim 3 wherein Q includes only carbon and hydrogen atoms.

6. The compound of claim 5 wherein Q is 2-naphthalenyl.

7. The compound of claim 1 wherein Q is pyrenyl, purinyl, acridinyl, xanthenyl, fluorenyl, phenanthrenyl, anthracenyl, quinolinyl, isoquinolinyl, naphthalenyl, perylenyl, phenanthridinyl, phenazinyl, anthraquinonyl, azulenyl or dibenzofuranyl.

8. The compound of claim 1 wherein $R_1$ and $R_2$ are each H.

9. The compound of claim 1 wherein $R_1$ and $R_2$ are each, independently, a hydroxyl protecting group.

10. The compound of claim 1 wherein one of $R_1$ and $R_2$ is H and the other of $R_1$ and $R_2$ is a hydroxyl protecting group.

11. The compound of claim 1 wherein $R_3$ and $R_4$ are each, independently, $C_1$-$C_6$ alkyl.

12. The compound of claim 11 wherein $R_3$ and $R_4$ are each methyl.

13. The compound of claim 1 wherein:
- $R_1$ is a hydroxyl protecting group;
- $R_2$ is H; and
- $R_3$ and $R_4$ are each methyl.

14. The compound of claim 13 wherein Q is 2-napthalenyl.

15. The compound of claim 1 having the configuration:

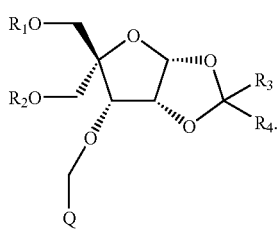

16. The compound of claim 15 having the formula:

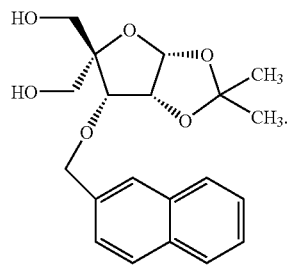

17. The compound of claim 1 having the configuration:

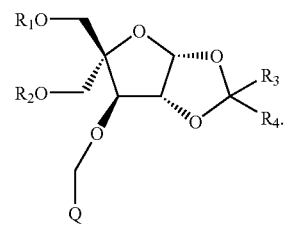

18. The compound of claim 17 having the formula:

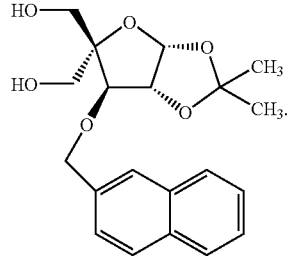

19. A method of preparing a bicyclic nucleoside comprising a bridge between the 4' and 2' ring carbons using the compound of claim 1.

20. The method of claim 19 wherein said bridge comprises from 2 to 3 bivalent subunits.

21. The method of claim 20 wherein said bivalent subunits are each, independently, selected from —$CR_5R_6$—, —C(=O)—, —$NR_5$, and —O—, wherein each $R_5$ and $R_6$ is, independently, H, $C_1$-$C_6$ alkyl, substituted $C_1$-$C_6$ alkyl, a substituted heteroatom (O, S or N) or a protecting group.

22. The method of claim 21 wherein said bivalent subunits form a bridge having the formula:
—$CH_2$—O—, —$(CH_2)_2$—O—, —$CH_2$—O—$N(R_5)$—, —$CH_2$—$N(R_5)$—O—, $CH_2$—$N(R_5)$—$CH_2$—, —CH$(R_5)$—O—, —$CH_2$—$N(R_5)$—$N(R_5)$— or —C(=O)—$N(R_5)$—$CH_2$—.

23. The method of claim 19 wherein said compound has the configuration:
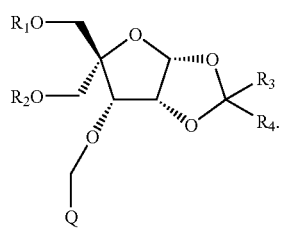
24. The method of claim 23 wherein said compound has the formula:
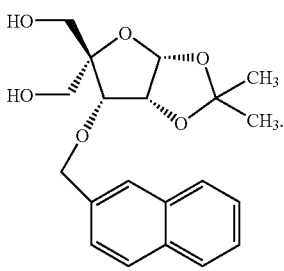
25. The method of claim 19 wherein said compound has the configuration:
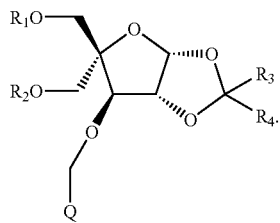
26. The method of claim 25 wherein said compound has the formula:
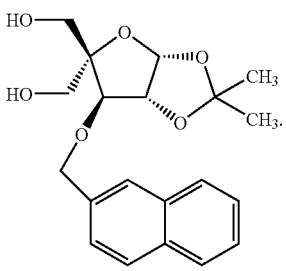
* * * * *